(12) United States Patent
Lv et al.

(10) Patent No.: US 10,377,725 B2
(45) Date of Patent: Aug. 13, 2019

(54) PHENYL AMINO PYRIMIDINE COMPOUND OR POLYMORPH OF SALT THEREOF

(71) Applicant: Suzhou Zelgen Biopharmaceuticals Co., Ltd., Kunshan Suzhou, Jiangsu (CN)

(72) Inventors: Binhua Lv, Jiangsu (CN); Chengwei Li, Jiangsu (CN); Dan Xiao, Jiangsu (CN)

(73) Assignee: Suzhou Zelgen Biopharmaceuticals Co., Ltd., Kunshan Suzhou, Jiangsu (CN)

( * ) Notice: Subject to any disclaimer, the term of this patent is extended or adjusted under 35 U.S.C. 154(b) by 0 days.

(21) Appl. No.: 15/739,254

(22) PCT Filed: Jun. 24, 2016

(86) PCT No.: PCT/CN2016/087092
§ 371 (c)(1),
(2) Date: Dec. 22, 2017

(87) PCT Pub. No.: WO2016/206633
PCT Pub. Date: Dec. 29, 2016

(65) Prior Publication Data
US 2018/0179169 A1    Jun. 28, 2018

(30) Foreign Application Priority Data
Jun. 26, 2015   (CN) .......................... 2015 1 0364281

(51) Int. Cl.
*C07D 239/42*   (2006.01)
*C07D 265/30*   (2006.01)
*A61K 31/5377*  (2006.01)

(52) U.S. Cl.
CPC ........ *C07D 265/30* (2013.01); *A61K 31/5377* (2013.01); *C07D 239/42* (2013.01)

(58) Field of Classification Search
CPC .......................... C07D 239/42; A61K 31/5377
USPC ........................................ 544/122; 514/235.8
See application file for complete search history.

(56) References Cited

FOREIGN PATENT DOCUMENTS

| WO | 2008109943 A1 | 9/2008 |
| WO | 2014110189 A1 | 7/2014 |
| WO | 2014114274 A1 | 7/2014 |

OTHER PUBLICATIONS

Morissette et al., High-throughput crystallization: polymorphs, salts, co-crystals and solvates of pharmaceutical solids, Advanced Drug Delivery Reviews, 56 (2004), pp. 275-300.*
Tsygankov, Non-Receptor Protein Tyrosine Kinases, Frontiers in Bioscience, 8, pp. 595-635 (2003).*
Int'l Search Report dated Sep. 23, 2016 in Int'l Application No. PCT/CN2016/087092.

* cited by examiner

*Primary Examiner* — Deepak R Rao
(74) *Attorney, Agent, or Firm* — Panitch Schwarze Belisario & Nadel LLP

(57) ABSTRACT

The present invention relates to a phenyl amino pyrimidine compound or a polymorph of a salt thereof, specifically, to N-(cyanomethyl)-4-(2-((4-(2',2',6',6'-d$_4$-morpholino)phenyl)amino)pyrimidin-4-yl)benzamide, or a pharmaceutically acceptable salt thereof, or a polymorph of a solvate thereof, that is, a compound shown in formula I or salt thereof, or a polymorph of a solvate thereof. The polymorph is suitable for preparing a pharmaceutical composition for suppressing non-receptor tyrosine kinases (such as JAK kinase).

15 Claims, 10 Drawing Sheets

PHENYL AMINO PYRIMIDINE COMPOUND OR POLYMORPH OF SALT THEREOF

CROSS REFERENCE TO RELATED APPLICATIONS

This application is a Section 371 of International Application No. PCT/CN2016/087092, which was published on Dec. 29, 2016 in the Chinese language, under International Publication No. WO2016/206633, which claims priority under 35 U.S.C. § 119(b) to Chinese Patent Application No. 201510364281.3 filed on Jun. 26, 2015, the disclosures of which are incorporated herein by reference in their entireties.

TECHNICAL FIELD

The present invention relates to the field of medicine, and in particular, to polymorphs of a phenylaminopyrimidine compound or a salt thereof, and more particularly, to polymorphs of N-(cyanomethyl)-4-(2-((4-(2',2',6',6'-d$_4$-morpholino)phenyl)amino)pyrimidin-4-yl)benzamide or a pharmaceutically acceptable salt thereof.

BACKGROUND

The structure of N-(cyanomethyl)-4-(2-((4-(2',2',6',6'-d$_4$-morpholino)phenyl)amino)pyrimidin-4-yl)benzamide is shown as formula I:

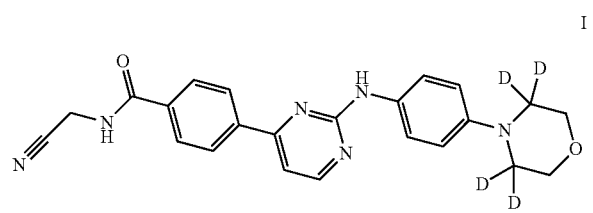 [SMILES: [2H]C1([2H])COCC([2H])([2H])N1c1ccc(Nc2nccc(-c3ccc(C(=O)NCC#N)cc3)n2)cc1]

The compound of formula I, with a molecular formula of $C_{23}H_{18}D_4N_6O_2$ and a molecular weight of 418.49 is a class of inhibitors of non-receptor tyrosine kinases (such as JAK kinases) and is suitable for preparing drugs for the treatment/prevention of cancer, myeloproliferative disorders, inflammation, and other related diseases.

Different crystal forms and salt forms of a drug might affect its dissolution, absorption in vivo, thereby affecting its clinical therapeutic effect and safety to a certain extent. In particular, for some slightly soluble solid or semisolid oral preparations, the influence of crystal forms is huge. There are no studies on polymorphs of compound I up to now, and no polymorph of compound I has been developed yet.

Therefore, it is necessary to develop polymorphs of compound I.

SUMMARY OF INVENTION

The purpose of the present invention is to provide polymorphs of compound I or a pharmaceutically acceptable salt thereof or a solvate thereof.

In the first aspect, a polymorph is provided and the polymorph is a polymorph of compound I or a pharmaceutically acceptable salt thereof or a solvate thereof,

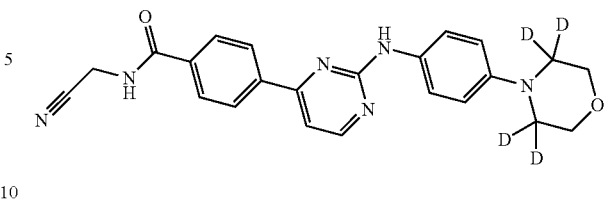

In another preferred embodiment, the pharmaceutically acceptable salt is hydrochloride.

In another preferred embodiment, in the hydrochloride of compound I, the molar ratio of compound I and hydrochloric acid is about 1:1 or 1:2.

In another preferred embodiment, the solvate is a monohydrate of the hydrochloride of compound I.

In another preferred embodiment, the polymorph is polymorph I of the hydrochloride of compound I, wherein the polymorph I has 3 or more than 3 characteristic peaks in X-ray powder diffraction pattern selected from the group consisting of 5.426±0.2°, 9.9851±0.2°, 13.424±0.2°, 14.765±0.2°25.148±0.2° and 26.566±0.2°.

In another preferred embodiment, the polymorph I has characteristic peaks in X-ray powder diffraction pattern selected from the group consisting of 8.827±0.2°, 15.537±0.2°, 17.193±0.2°, 19.268±0.2°, 20.862±0.2° and 30.282±0.2°.

In another preferred embodiment, the polymorph I has characteristic peaks in X-ray powder diffraction as essentially shown in FIG. 1a.

In another preferred embodiment, the polymorph I has a maximum peak at 233.19° C.±2° C. (or ±1° C., or ±0.5° C.) in differential scanning calorimetry pattern.

In another preferred embodiment, the polymorph I has a differential scanning calorimetry (DSC) pattern as essentially shown in FIG. 1b.

In another preferred embodiment, in the polymorph I, the molar ratio of compound I and hydrochloric acid is about 1:2.

In another preferred embodiment, the polymorph is polymorph II of a solvate of the hydrochloride of compound I, wherein the polymorph II has 3 or more than 3 characteristic peaks in X-ray powder diffraction pattern selected from the group consisting of 17.249±0.2°, 19.224±0.2°, 23.885±0.2° and 29.488±0.2°.

In another preferred embodiment, the polymorph H has characteristic peaks in X-ray powder diffraction pattern selected from the group consisting of 7.578±0.2°, 15.181±0.2°, 18.515±0.2°, 22.603±0.2°, 25.581±0.2° and 27.003±0.2°.

In another preferred embodiment, the polymorph II has characteristic peaks in X-ray powder diffraction as essentially shown in FIG. 2a.

In another preferred embodiment, the polymorph II has maximum peaks at 166.66° C.±2° C. (or ±1° C., or ±0.5° C.), 207.84° C.±2° C. (or ±1° C., or ±0.5° C.) and 240.84° C.±2° C. (or ±1° C., or ±0.5° C.) in differential scanning calorimetry pattern.

In another preferred embodiment, the polymorph II has a differential scanning calorimetry (DSC) pattern as essentially shown in FIG. 3b.

In another preferred embodiment, in the polymorph II, the molar ratio of compound I, hydrochloric acid and water is about 1:2:1.

In another preferred embodiment, the polymorph II is a monohydrate of the dihydrochloride of compound I.

In another preferred embodiment, the polymorph is polymorph III of the hydrochloride of compound I, wherein the polymorph III has 3 or more than 3 characteristic peaks in X-ray powder diffraction pattern selected from the group consisting of 15.178±0.2°, 20.7051±0.2°, 26.3901±0.2° and 28.0881±0.2°.

In another preferred embodiment, the polymorph III also has characteristic peaks in X-ray powder diffraction pattern selected from the group consisting of 13.305±0.2°, 16.204±0.2°, 16.953±0.2°, 18.809±0.2°, 20.073±0.2°, 22.937±0.2°, 25.958±0.2° and 31.837±0.2°.

In another preferred embodiment, the polymorph HI has characteristic peaks in X-ray powder diffraction as essentially shown in FIG. 3a.

In another preferred embodiment, the polymorph HI has a maximum peak at 249.49° C.±2° C. (or ±1° C., or ±0.5° C.) in differential scanning calorimetry pattern.

In another preferred embodiment, the polymorph III has a differential scanning calorimetry (DSC) pattern as essentially shown in FIG. 3b.

In another preferred embodiment, in the polymorph III, the molar ratio of compound I to hydrochloric acid is about 1:1.

In another preferred embodiment, the polymorph is polymorph IV of the hydrochloride of compound I, wherein the polymorph IV has 3 or more than 3 characteristic peaks in X-ray powder diffraction pattern selected from the group consisting of 12.493±0.2°14.447±0.2°, 17.627±0.2°, 19.519±0.2°, 23.231±0.2°, 23.805±0.2° and 24.831±0.2°.

In another preferred embodiment, the polymorph IV also has characteristic peaks in X-ray powder diffraction pattern selected from the group consisting of 4.422±0.2°, 12.986±0.2°, 17.074±0.2°, 22.344±0.2°, 24.396±0.2°, 25.778±0.2°, 28.166±0.2°, 28.738±0.2°, 29.607±0.2° and 31.741±0.2°.

In another preferred embodiment, the polymorph IV has characteristic peaks in X-ray powder diffraction as essentially shown in FIG. 4a.

In another preferred embodiment, the polymorph IV has a maximum peak at 242.73° C.±2° C. (or +1° C., or ±0.5° C.) in differential scanning calorimetry pattern.

In another preferred embodiment, the polymorph IV has a differential scanning calorimetry (DSC) pattern as essentially shown in FIG. 4b.

In another preferred embodiment, in the polymorph IV, the molar ratio of compound I to hydrochloric acid is about 1:1.

In another preferred embodiment, the polymorph is polymorph V of compound I, wherein the polymorph V has 3 or more than 3 characteristic peaks in X-ray powder diffraction pattern selected from the group consisting of 13.621±0.2°, 18.634±0.2°, 20.331±0.2°, 21.675±0.2°, 22.621±0.2° and 28.048±0.2°.

In another preferred embodiment, the polymorph V also has characteristic peaks in X-ray powder diffraction pattern selected from the group consisting of 7.263±0.7°, 17.647±0.7°, 21.179±0.2°, 23.509±0.2°, 24.857±0.2°, 25.148±0.2°, 27.179±0.2°, and 30.181±0.2°.

In another preferred embodiment, the polymorph V has characteristic peaks in X-ray powder diffraction as essentially shown in FIG. 5a.

In another preferred embodiment, the polymorph V has a maximum peak at 258.31° C.±2° C. (or ±1° C., or ±0.5° C.) in differential scanning calorimetry pattern.

In another preferred embodiment, the polymorph V has a differential scanning calorimetry (DSC) pattern as essentially shown in FIG. 5b.

In another preferred embodiment, the polymorph is polymorph VI of compound I, wherein the polymorph VI has 3 or more than 3 characteristic peaks in X-ray powder diffraction pattern selected from the group consisting of 4.084±0.2°, 18.832±0.2°, 19.542±0.2°, 20.529±0.2°, and 26.468±0.2°.

In another preferred embodiment, the polymorph VI also has one or more characteristic peaks in X-ray powder diffraction pattern selected from the group consisting of 12.277±0.2°, 17.589±0.2°, 20.032±0.2°, 21.003±0.2°, 24.870±0.2° and 27.597±0.2°.

In another preferred embodiment, the polymorph VI has characteristic peaks in X-ray powder diffraction as essentially shown in FIG. 6a.

In another preferred embodiment, the polymorph VI has a maximum peak at 259.38° C.±2° C. (or ±1° C., or ±0.5° C.) in differential scanning calorimetry pattern.

In another preferred embodiment, the polymorph VI has a differential scanning calorimetry (DSC) pattern as essentially shown in FIG. 6b.

In the second aspect, a use of the polymorphs according to the first aspect of the present invention is provided, for the preparation of a pharmaceutical composition of non-receptor tyrosine kinases (such as JAK kinases).

In another preferred embodiment, the pharmaceutical composition is used for treating and preventing cancer, myeloproliferative and inflammatory diseases.

In the third aspect, a pharmaceutical composition is provided, comprising (a) the polymorphs according to the first aspect of the present invention; and (b) a pharmaceutically acceptable carrier.

In the fourth aspect, a method for preparing the polymorphs according to the first aspect of the present invention is provided, comprising a step of: compound I is salified with an acid and crystallized in an inert solvent, or recrystallizing compound I or pharmaceutically acceptable salts thereof or solvates thereof in an inert solvent, thereby obtaining the polymorphs according to the first aspect of the present invention.

In another preferred embodiment, the recrystallizing is performed with or without addition of seed crystal.

In another preferred embodiment, the acid is hydrochloric acid.

In another preferred embodiment, the method for preparing polymorph I comprises a step of: compound I is salified with hydrochloric acid and crystallized in an inert solvent, thereby obtaining the polymorph I of the present invention.

In another preferred embodiment, the inert solvent is selected from the group consisting of: ethanol, methanol, isopropanol, acetic acid, formic acid, water, or a combination thereof.

In another preferred embodiment, the molar ratio of compound I and the hydrochloric acid is about 1:2-1:5.

In another preferred embodiment, the method for preparing polymorph I comprises a step of: in ethanol and/or methanol, compound I is salified with hydrochloric acid and crystallized, thereby obtaining the polymorph I of the present invention.

In another preferred embodiment, the method for preparing polymorph I comprises a step of: in a mixed solvent of acetic acid and ethanol, compound I is salified with hydrochloric acid and crystallized, thereby obtaining the polymorph I of the present invention.

In another preferred embodiment, the volume ratio of ethanol to methanol is 1:50-50:1.

In another preferred embodiment, the volume ratio of acetic acid to ethanol is 1:5-5:1, preferably, 1:2-2:1.

In another preferred embodiment, the method for preparing polymorph II comprises a step of: in a mixed solvent of dimethylsulfoxide and ethanol, dimethylsulfoxide and methanol, or dimethylsulfoxide and acetone, compound I is salified with hydrochloric acid and crystallized, thereby obtaining the polymorph II of the present invention.

In another preferred embodiment, the volume ratio of dimethylsulfoxide to ethanol is 1:5-5:1; the volume ratio of dimethylsulfoxide to methanol is 1:5-5:1; the volume ratio of dimethylsulfoxide to acetone is 1:5-5:1.

In another preferred embodiment, the method for preparing polymorph II comprises a step of: suspending the obtained polymorph I in a mixed solvent of acetone and water and stirring, thereby obtaining the polymorph II of the present invention.

In another preferred embodiment, the volume ratio of acetone to water is 10:1-50:1, preferably, 20:1.

In another preferred embodiment, the method for preparing polymorph II comprises a step of: placing the obtained polymorph. I in a high humidity (such as 90% of the humidity) environment for a period of time, thereby obtaining the polymorph II of the present invention.

In another preferred embodiment, the method for preparing polymorph II comprises steps of:
(i) suspending the obtained polymorph I in methanol, thereby forming a mixture A1; and
(ii) adding hydrochloric acid to the mixture A1, and crystallizing, thereby obtaining the polymorph.

In another preferred embodiment, in step (i), the concentration of hydrochloric acid is 0.5-3M, preferably, 0.7-2M, more preferably, 0.8-1.2M.

In another preferred embodiment, the crystallizing is performed with stirring.

In another preferred embodiment, the stirring time is 4-48 h, preferably 6-30 h, more preferably 10-24 h.

In another preferred embodiment, in step (ii), the molar ratio of polymorph I to the hydrochloric acid is about 10:1-1:1, preferably, 8:1-2:1, more preferably, 6:1-3:1.

In another preferred embodiment, the method for preparing polymorph II comprises steps of:
(i) suspending compound I in methanol, thereby forming a mixture A2; and
(ii) adding hydrochloric acid to the mixture A2, once the mixture was upon dissolved completely after stirring, immediately adding the seed crystal and water, thereby forming the polymorph II.

In another preferred embodiment, in step (ii), the concentration of hydrochloric acid is 6M to saturated, preferably 8-12 M.

In another preferred embodiment, the molar ratio of compound I to the hydrochloric acid is about 1:1.8-1:3, preferably, 1:1.9-1:2.5, preferably, 1:2.0-1:2.4.

In another preferred embodiment, the method for preparing polymorph III comprises a step of: in a mixed solvent of N-methylpyrrolidone and ethanol, compound I is salified with hydrochloric acid and crystallized, thereby obtaining the polymorph III of the present invention.

In another preferred embodiment, the volume ratio of N-methylpyrrolidone to ethanol is 1:1-1:10.

In another preferred embodiment, the method for preparing polymorph III comprises a step of: in absolute methanol, recrystallizing the obtained polymorph II, thereby obtaining the polymorph III of the present invention.

In another preferred embodiment, the method for preparing polymorph III comprises a step of: stirring the formed mixture of compound I, hydrochloric acid and methanol, and crystallizing, thereby obtaining the polymorph III of the present invention.

In another preferred embodiment, the concentration of hydrochloric acid is 6M to saturated, preferably 8-12 M.

In another preferred embodiment, the molar ratio of compound I to the hydrochloric acid is about 1:0.9-1:1.2.

In another preferred embodiment, the methanol comprises absolute methanol.

In another preferred embodiment, the method for preparing polymorph IV comprises a step of: recrystallizing the obtained polymorph I in water, thereby obtaining the polymorph IV of the present invention.

In another preferred embodiment, the method for preparing polymorph IV comprises a step of: compound I is salified in an aqueous hydrochloric acid solution, and crystallized, thereby obtaining the polymorph IV of the present invention.

In another preferred embodiment, the method for preparing polymorph IV comprises a step of: suspending the obtained polymorph H in a mixed solvent of methanol and water and stirring, thereby obtaining the polymorph IV of the present invention.

In another preferred embodiment, the volume ratio of methanol to water is 5:1-1:10.

In another preferred embodiment, the method for preparing polymorph V comprises a step of: recrystallizing compound I in a mixed solvent of N,N-dimethylformamide (or DMSO) and water, thereby obtaining the polymorph V of the present invention.

In another preferred embodiment, the volume ratio of N,N-dimethylformamide (or DMSO) to water is 1:2-1:10, preferably, 1:3.

In another preferred embodiment, the method for preparing polymorph VI comprises a step of: stirring the obtained polymorph II in a pH 6.8 phosphate buffer, thereby obtaining the polymorph VI of the present invention.

In the fifth aspect, a preparation method for the polymorph H is provided, comprising steps of:
(1) mixing compound I and a first solvent to form a first solvent containing compound I;

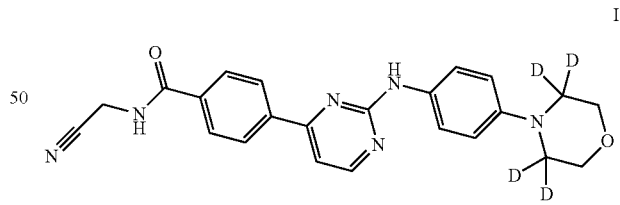

I (2) adding hydrochloric acid and acetone to the first solvent to form a first mixture;
(3) stirring the first mixture, thereby precipitating a solid;
(4) separating and obtaining the solid precipitated from the previous step;
(5) mixing the separated solid and the mixed solvent of acetone/water to form a second mixture; and
(6) separating the crystallized polymorph II from the second mixture.

In another preferred embodiment, in the first mixture, the molar ratio of compound I to the hydrochloric acid is about 1:1.8-1:3, preferably, 1:1.9-1:2.5 preferably, 1:2.0-1:2.4.

In another preferred embodiment, in the mixed solvent of acetone/water, the volume ratio of acetone to water is 8:1-50:1, preferably, 10:1-30:1, preferably, 12:1-25:1.

In another preferred embodiment, the first solvent is selected from the group consisting of: dimethylsulfoxide, N,N-dimethylformamide, N-methylpyrrolidone, acetic acid, or a combination thereof.

In another preferred embodiment, the method has one or more characteristics selected from the group consisting of:

(a) in step (3), the temperature is 4-35° C., preferably, 5-30° C., more preferably, 10-25° C.;

(b) in step (5), the temperature is 4-35° C., preferably, 5-30° C., more preferably, 10-25° C.;

(c) in step (6), the temperature is 4-35° C., preferably 5-30° C., more preferably, 10-25° C.;

(d) in step (2), the hydrochloric acid and acetone are added in the form of an acetone solution of hydrochloric acid; preferably, in the acetone solution of hydrochloric acid, the content of HCl is 0.1-20 wt %; preferably, 0.5-15 wt %, more preferably, 1-10 wt % (such as 4 wt % or 5 wt %).

It should be understood that in the present invention, any of the technical features specifically described above and below (such as in the Examples) can be combined with each other, thereby constituting new or preferred technical solutions which will not redundantly be described one by one herein.

DETAILED DESCRIPTION OF INVENTION

Figure 1A:
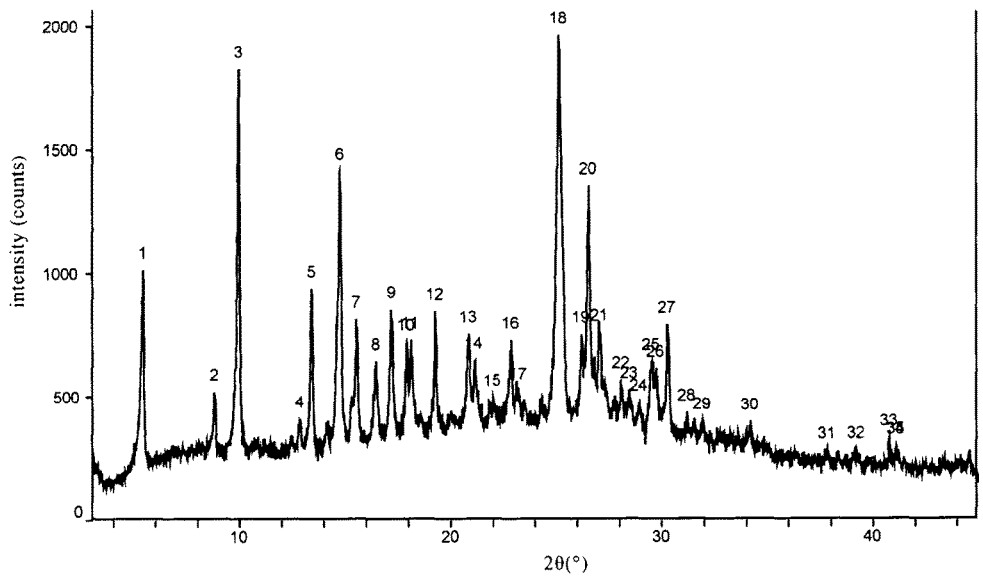
FIG. 1a shows an X-ray powder diffraction pattern of polymorph I.

Through long-term and intensive studies, the inventors have unexpectedly discovered various polymorphs of compound I or pharmaceutically acceptable salts thereof, or solvates thereof, which have a better drug bioavailability, and are highly pure and very stable, and suitable for preparing a pharmaceutical composition inhibiting non-receptor tyrosine kinases (such as JAK kinases), and are therefore more beneficial for the treatment of cancer, myeloproliferative and inflammatory diseases. Moreover, the polymorphs of the present invention are not prone to floating, easy for collection so that it is easy to avoid wasting and helpful to protect the health of operators in the manufacturing process of a drug, such as subpackage. Based on this discovery, the inventors have completed the present invention.

As used herein, "compound I" refers to N-(cyanomethyl)-4-(2-((4-(2',2',6',6'-$d_4$-morpholino)phenyl)amino)pyrimidin-4-yl)benzamide as shown in formula I.

As used herein, "inert solvent" refers to methanol, ethanol, isopropanol, dimethylsulfoxide, N-methylpyrrolidone, N,N-dimethylformamide, acetone, acetonitrile, acetic acid, formic acid, n-hexane, n-heptane, toluene, tetrahydrofuran, ethyl acetate, 1,4-dioxane, methyl t-butyl ether, water or a mixture of the above solvents.

N-(cyanomethyl)-4-(2-((4-(2',2',6',6'-$d_4$-morpholino)phenyl)amino)pyrimidin-4-yl)benzamide hydrochloride The N-(cyanomethyl)-4-(2-((4-(2',2',6',6'-$d_4$-morpholino)phenyl)amino)pyrimidin-4-yl)benzamide hydrochloride of the present invention comprises various forms of the hydrochloride of compound I.

Preferably, it is the N-(cyanomethyl)-4-(2-((4-(2',2',6',6'-$d_4$-morpholino)phenyl)amino)pyrimidin-4-yl)benzamide dihydrochloride, which refers to a salt wherein the molar ratio of compound I to hydrochloric acid is 1:2; or it is the N-(cyanomethyl)-4-(2-((4-(2',2',6',6'-$d_4$-morpholino)phenyl)amino)pyrimidin-4-yl)benzamide dihydrochloride monohydrate, which refers to a salt wherein the molar ratio of compound I to hydrochloric acid and water is 1:2:1.

it is the N-(cyanomethyl)-4-(2-((4-(2',2',6',6'-$d_4$-morpholino)phenyl)amino)pyrimidin-4-yl)benzamide monohydrochloride, which refers to a salt wherein the molar ratio of compound I to hydrochloric acid is 1:1.

Polymorph

Solid exists in either amorphous form or crystal form. In the case of crystal form, the molecules are localized in the three-dimensional lattice sites. When a compound is crystallized from a solution or slurry, it can be crystallized in a different arrangement lattice of spaces (this property is called "polymorphism") to form crystals with different crystalline forms, each of which is known as "polymorphs". Different polymorphs of a given substance may be different from each other in one or more physical properties, such as solubility and dissolution rate, true specific gravity, crystal form, accumulation mode, flowability and/or solid state stability, and so on.

Crystallization

The production-scale crystallization can be achieved by operating a solution so as to exceed the solubility limit of an interested compound. This can be accomplished through a variety of methods, for example, by dissolving a compound at a relatively high temperature, and then cooling the solution below a saturation limit, or reducing the liquid volume by boiling, atmospheric evaporation, vacuum drying or some other methods, the solubility of the interested compound can be reduced by adding an anti-solvent or a solvent in which the compound has a low solubility, or a mixture of such solvents. An alternative method is to reduce the solubility by adjusting the pH value. See Crystallization, Third Edition, J W Mullens, Butterworth-Heineman Ltd., 1993, ISBN 0750611294 for a detailed description of crystallization.

If salt formation and its crystallization are expected to occur simultaneously, and the solubility of salt is lower than the raw material in the reaction medium, then the salt can be crystallized directly by adding an appropriate acid or base. Likewise, in a medium in which the solubility of the desired final form is lower than that of reactant, the final product can be directly crystallized when the synthetic reaction is completed.

Optimization of crystallization may include addition of the crystal of desired form as a crystal seed into the crystallization medium. In addition, many crystallization methods use a combination of the above strategies. One way is to dissolve the interested compound in a solvent at a high temperature, then add an anti-solvent with an appropriate volume through a controlled mode, in order to make the system just below the saturation level. At this moment, the seed of desired form may be added (the integrity of the seed is kept), then crystallization is achieved by cooling the system.

As used herein, the term "room temperature" generally refers to 4-30° C., preferably, 20±5° C.

Polymorh of the Present Invention

As used herein, the term "polymorphs of the present invention" comprises polymorphs of compound I or pharmaceutically acceptable salts thereof (such as the hydrochloride), or various solvates thereof, and further comprises different polymorphs of the same hydrochloride or solvate.

Figure 7:
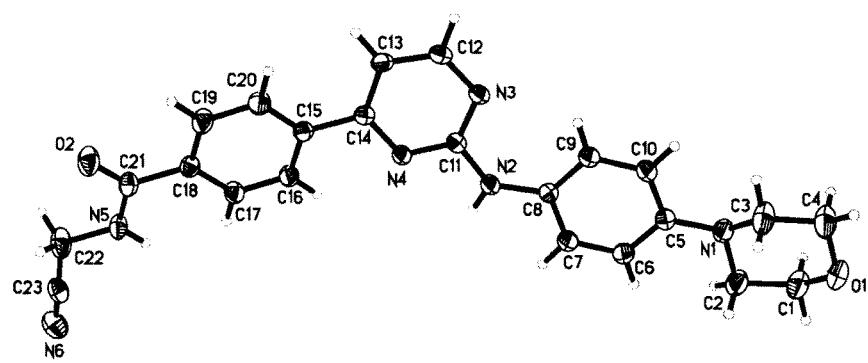
FIG. 7 shows the molecular structure of the polymorph of N-(cyanomethyl)-4-(2-((4-(2',2',6',6'-$d_4$-morpholino)phenyl)amino)pyrimidin-4-yl)benzamide.

The preferable polymorphs of the present invention include but are not limited to:
polymorph V of compound I;
polymorph VI of compound I;
polymorph I of the di hydrochloride of compound I;
polymorph II of the dihydrochloride monohydrate of compound I;
polymorphs III and IV of the monohydrochloride of compound I;
wherein in the polymorph I, the molar ratio of compound I to hydrochloric acid is 1:2; in the polymorph II, the molar ratio of compound I to hydrochloric acid and water is 1:2:1; in the polymorphs III and IV, the molar ratio of compound I to hydrochloric acid is 1:1.

Wherein the molecular formula of the crystal form of compound I is shown in FIG. 7.

Identification and Property of Polymorph

After preparing the polymorphs of compound I, the properties thereof are studied using the following various methods and instruments.

X-Ray Power Diffraction

The method of determining X-ray powder diffraction of the crystal form is known in the field. For example, the pattern is obtained by copper radiation target using an X-ray powder diffractometer of Rigaku D/max 2550VB/PC at a scanning rate of 2° per minute.

The polymorphs of the compound I of the present invention have a specific crystal form and have specific characteristic peaks in the X-ray powder diffraction (XRPD) pattern. The preferred are as follows:

(1) Polymorph I

The polymorph I has 3 or more than 3 characteristic peaks in X-ray powder diffraction selected from the group consisting of 5.426±0.2°, 9.985±0.2°, 13.424±0.2°, 14.765±0.2°, 25.148±0.2° and 26.566±0.2°.

In another preferred embodiment, the polymorph I has characteristic peaks in X-ray powder diffraction selected from the group consisting of 8.827±0.2°, 15.537±0.2°, 17.193±0.2°, 19.268±, 20.862±0.2° and 30.282±0.2°.

In another preferred embodiment, the polymorph I has an X-ray powder diffraction pattern as essentially shown in FIG. 1a.

(2) Polymorph II

The polymorph II has 3 or more than 3 characteristic peaks in X-ray powder diffraction selected from the group consisting of 17.249±0.2°, 19.224±0.2°, 23.885±0.2° and 29.488±0.2°. In another preferred embodiment, the polymorph II has characteristic peaks in X-ray powder diffraction selected from the group consisting of 7.578±0.2°, 15.181±0.2°, 18.515±0.2°, 22.603±0.2°, 25.581±0.2° and 27.003±0.2°. In another preferred embodiment, the polymorph II has an X-ray powder diffraction pattern as essentially shown in FIG. 2a.

(3) Polymorph III

The polymorph III has 3 or more than 3 characteristic peaks in X-ray powder diffraction selected from the group consisting of 15.178±0.2°, 20.705±0.2°, 26.390±0.2° and 28.088±0.2°. In another preferred embodiment, the polymorph III has characteristic peaks in X-ray powder diffraction selected from the group consisting of 13.305±0.2°, 16.2041±0.2°, 16.9531±0.2°, 18.809±0.2°, 20.073±0.2°, 22.937±0.2°, 25.958±0.2° and 31.837±0.2°. In another preferred embodiment, the polymorph HI has an X-ray powder diffraction pattern as essentially shown in FIG. 3a.

(4) Polymorph IV

The polymorph IV has 3 or more than 3 characteristic peaks in X-ray powder diffraction selected from the group consisting of 12.493±0.2°, 14.447±0.2°, 17.627±0.2°, 19.519±0.2°, 23.231±0.2°, 23.805±0.2° and 24.831±0.2°. In another preferred embodiment, the polymorph IV has characteristic peaks in X-ray powder diffraction selected from the group consisting of 4.422±0.2°, 12.986±0.2°, 17.074±0.2°, 22.344±0.2°, 24.396±0.2°, 25.778±0.2°, 28.166±0.2°, 28.738±0.2°, 29.607±0.2° and 31.741±0.2°. In another preferred embodiment, the polymorph IV has an X-ray powder diffraction pattern as essentially shown in FIG. 4a.

(5) Polymorph V

The polymorph V has 3 or more than 3 characteristic peaks in X-ray powder diffraction selected from the group consisting of 13.621±0.2°, 18.634±0.2°, 20.331±0.2°, 21.675±0.2°, 22.621±0.2° and 78.048±0.2°. In another preferred embodiment, the polymorph V has characteristic peaks in X-ray powder diffraction selected from the group consisting of 7.263±0.2°, 17.647±0.2°, 21.179±0.2°, 23.509±0.2°, 24.852±0.2°, 25.148±0.2°, 27.179±0.2° and 30.181±0.2°. In another preferred embodiment, the polymorph V has an X-ray powder diffraction pattern as essentially shown in FIG. 5a.

(6) Polymorph VI

The polymorph VI has 3 or more than 3 characteristic peaks in X-ray powder diffraction selected from the group consisting of 4.084±0.2°, 18.832±0.2°, 19.542±0.2°, 20.529±0.2°, and 26.468±0.2°. In another preferred embodiment, the polymorph VI has characteristic peaks in X-ray powder diffraction selected from the group consisting of 12.277±0.2°, 17.589±0.2<, 20.032±0.2°, 21.003±0.2°, 24.870±0.2° and 27.597±0.2°. In another preferred embodiment, the polymorph VI has an X-ray powder diffraction pattern as essentially shown in FIG. 6a.

Differential Scanning Calorimetry

Also called "differential scanning calorimetry analysis" (DSC) which refers to a technique that measures the relationship between energy difference of the measured substance and the reference substance and temperature during heating. Location, shape and number of peaks in DSC pattern are relevant to the properties of substance, so they can be used to identify a substance qualitatively. Generally, this method is use to detect the phase transition temperature, glass transition temperature, reaction heat and other parameters of a substance.

The method of DSC determination is known in the art. For example, differential scanning calorimeter of NETZSCH DSC 204 F1 can be used, at a heating rate of 10 degrees per minute, from 25° C. to 250° C., to obtain a DSC pattern of a crystal form.

The polymorphs of compound I of the present invention have specific characteristic peaks in differential scanning calorimetry (DSC) pattern.

(1) Polymorph I

The polymorph I has a maximum peak at 233.19° C.±2° C. (or ±1° C., or ±0.5° C.) in DSC pattern.

Figure 1B:
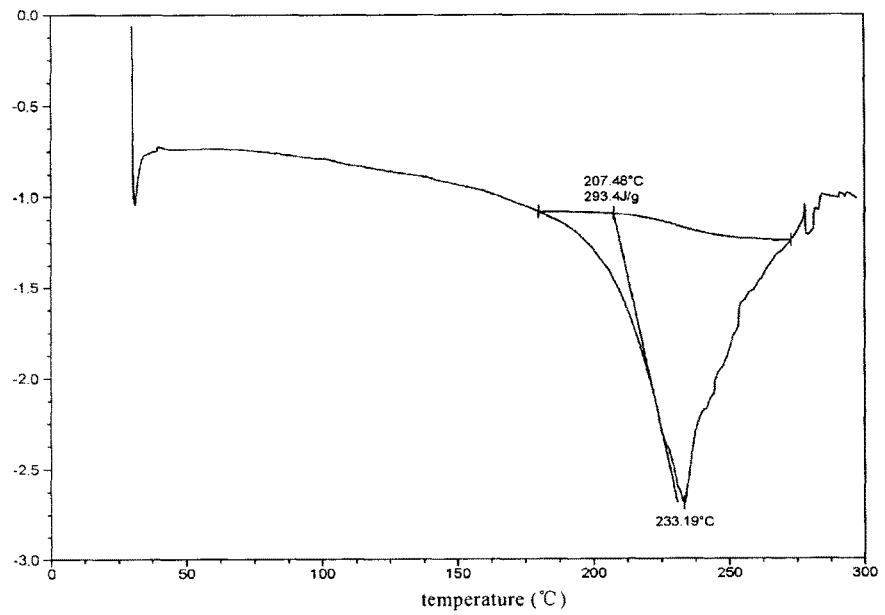
FIG. 1b shows a differential scanning calorimetry pattern of polymorph I.

In another preferred embodiment, the polymorph I has a differential scanning calorimetry(DSC) pattern substantially as shown in FIG. 1b.

(2) Polymorph II

The polymorph II has a maximum peaks at 166.66° C.±2° C. (or ±1° C., or ±0.5° C.) in DSC pattern.

Figure 2A:
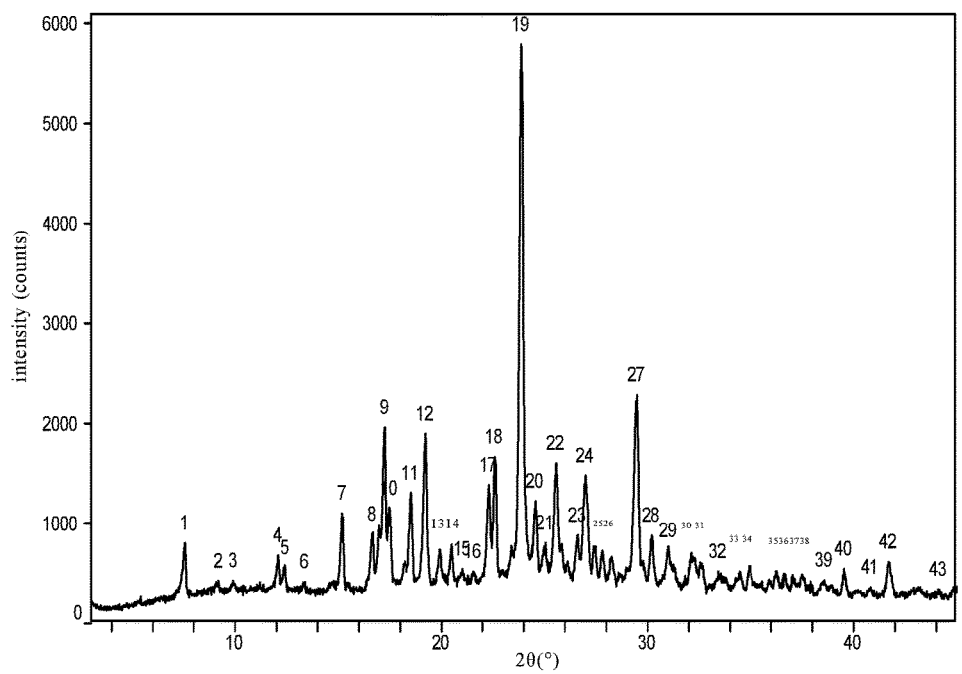
FIG. 2a shows an X-ray powder diffraction pattern of polymorph II.
Figure 2B:
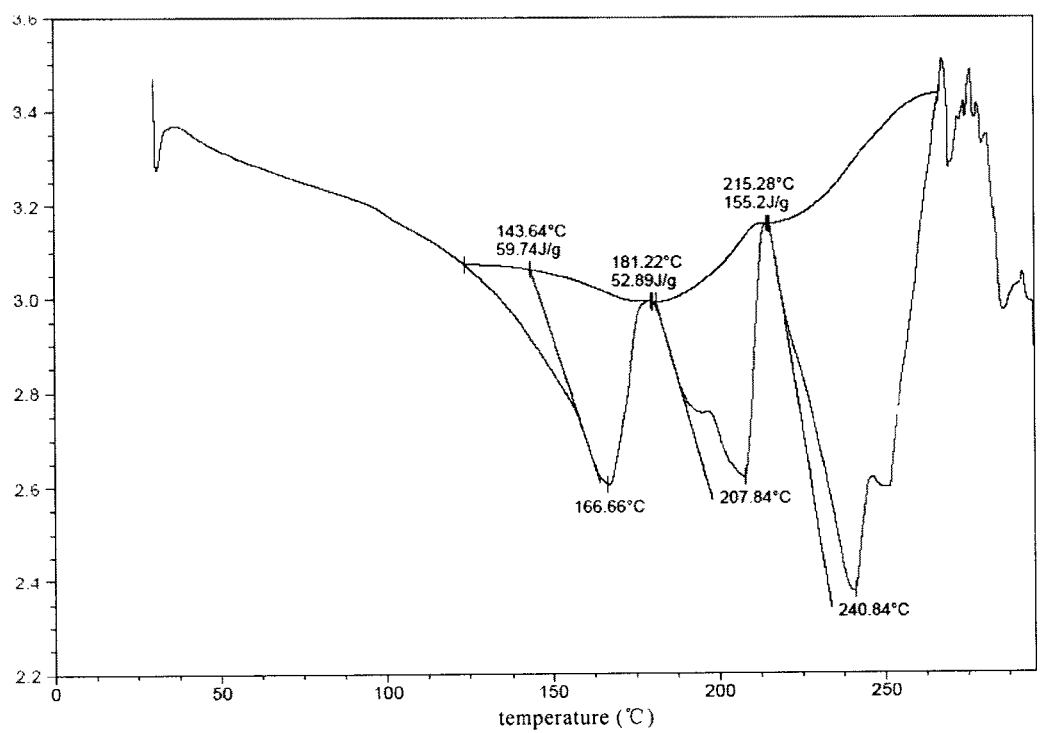
FIG. 2b shows a differential scanning calorimetry pattern of polymorph II.

In another preferred embodiment, the polymorph II has a DSC pattern as essentially shown in FIG. 2b.

(3) Polymorph

The polymorph III has a maximum peaks at 24949° C.±2° C. (or ±1° C., or ±0.5° C.) in DSC pattern.

Figure 3A:
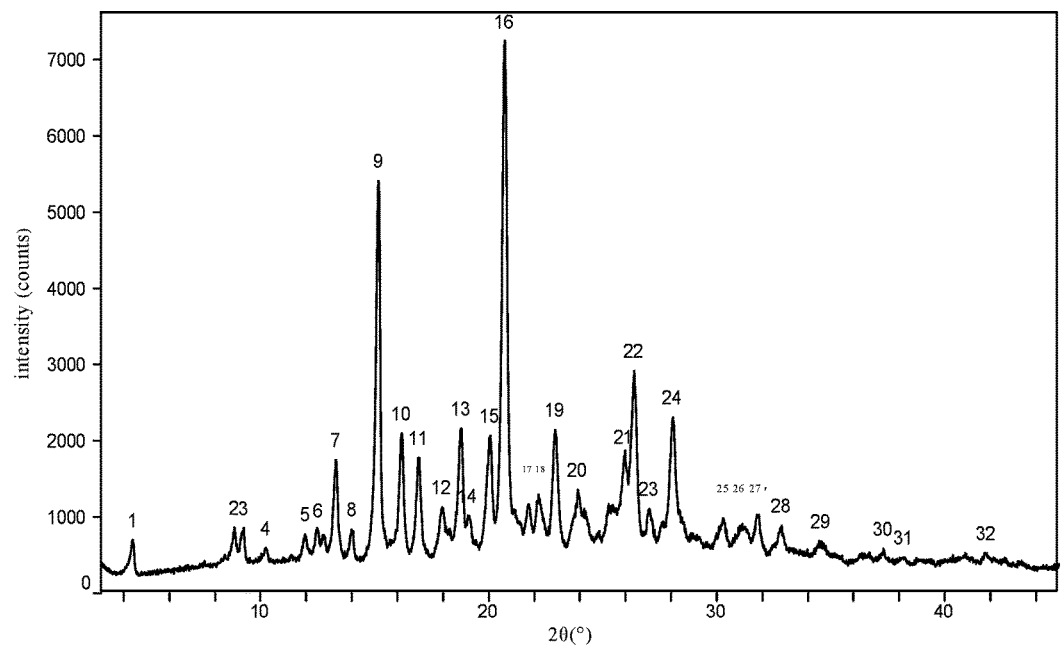
FIG. 3a shows an X-ray powder diffraction pattern of polymorph III.
Figure 3B:
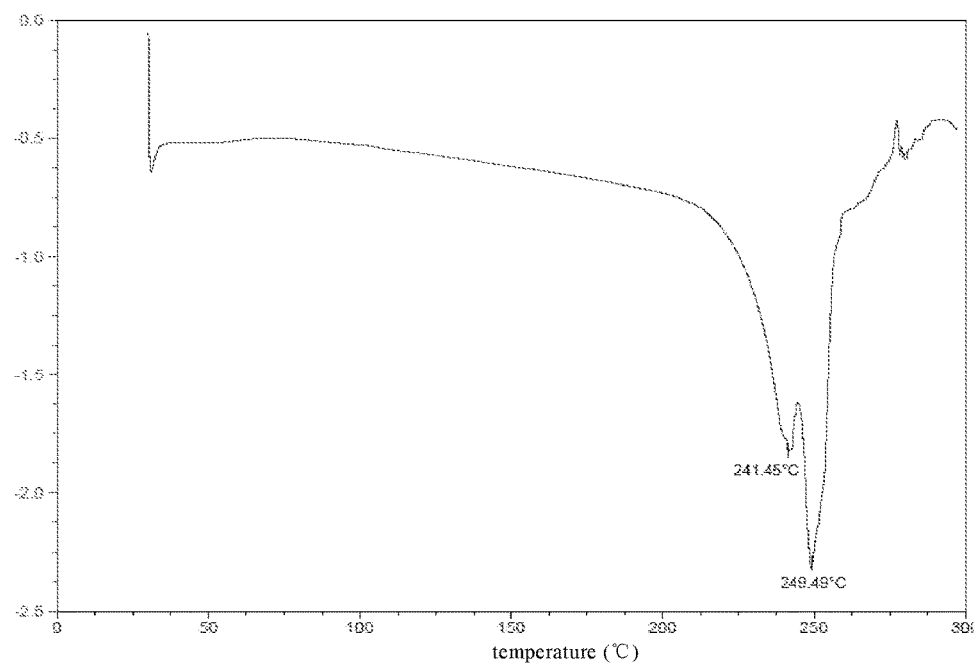
FIG. 3b shows a differential scanning calorimetry pattern of polymorph III.

In another preferred embodiment, the polymorph III has a DSC pattern as essentially shown in FIG. 3b.

(4) Polymorph IV

The polymorph IV has a maximum peaks at 242.73° C.±2° C. (or ±1° C., or ±0.5° C.) in DSC pattern.

Figure 4A:
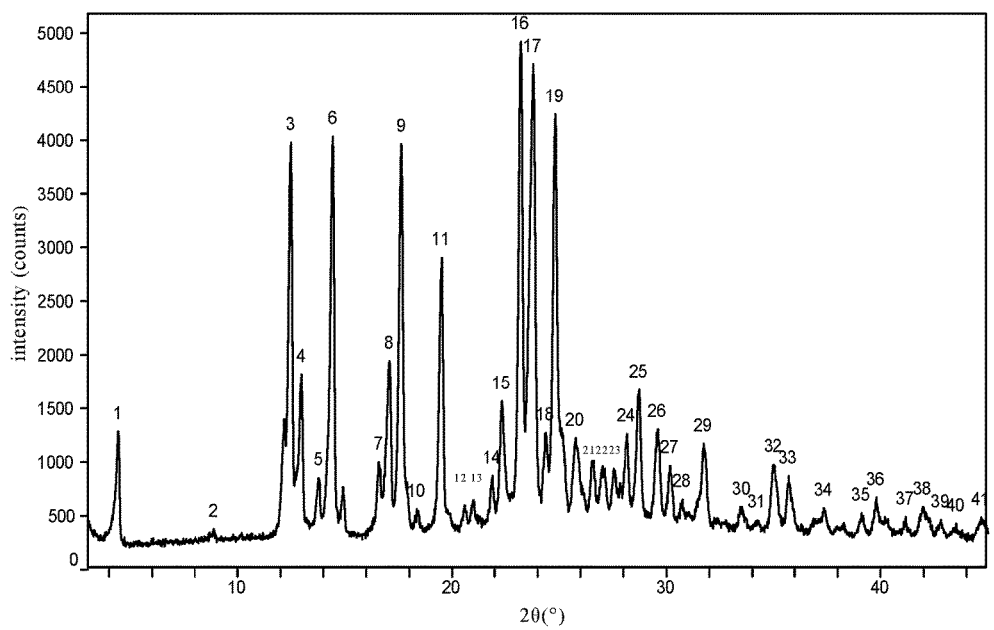
FIG. 4a shows an X-ray powder diffraction pattern of polymorph IV.
Figure 4B:
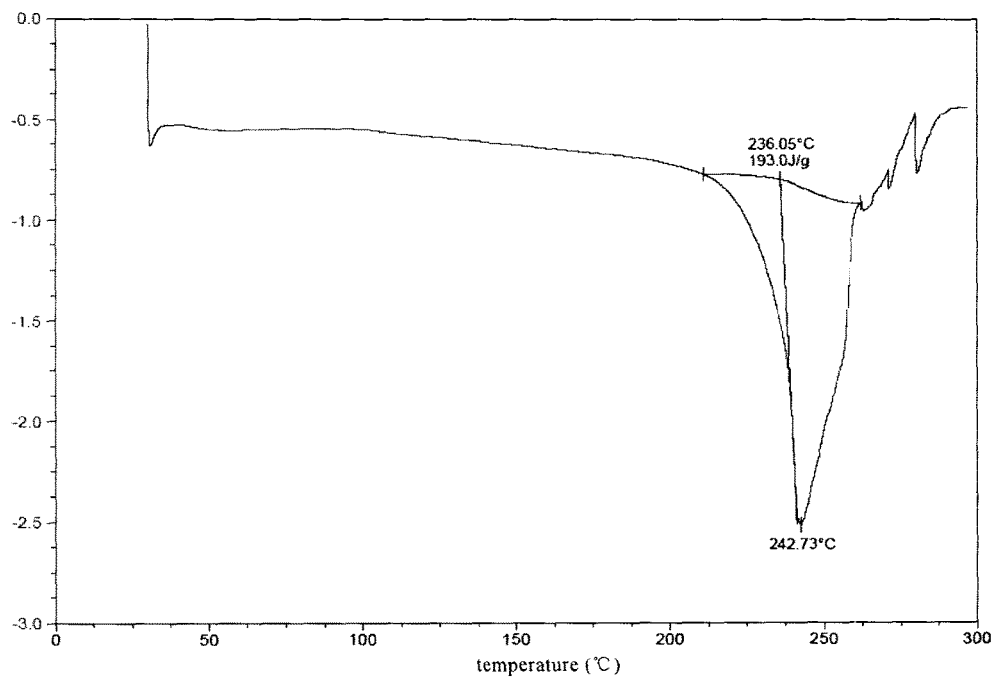
FIG. 4b shows a differential scanning calorimetry pattern of polymorph IV.

In another preferred embodiment, the polymorph IV has a DSC pattern as essentially shown in FIG. 4b.

(5) Polymorph V

The polymorph V has a maximum peak at 258.31° C.±2° C. (or ±1° C., or ±0.5° C.) in DSC pattern.

Figure 5A:
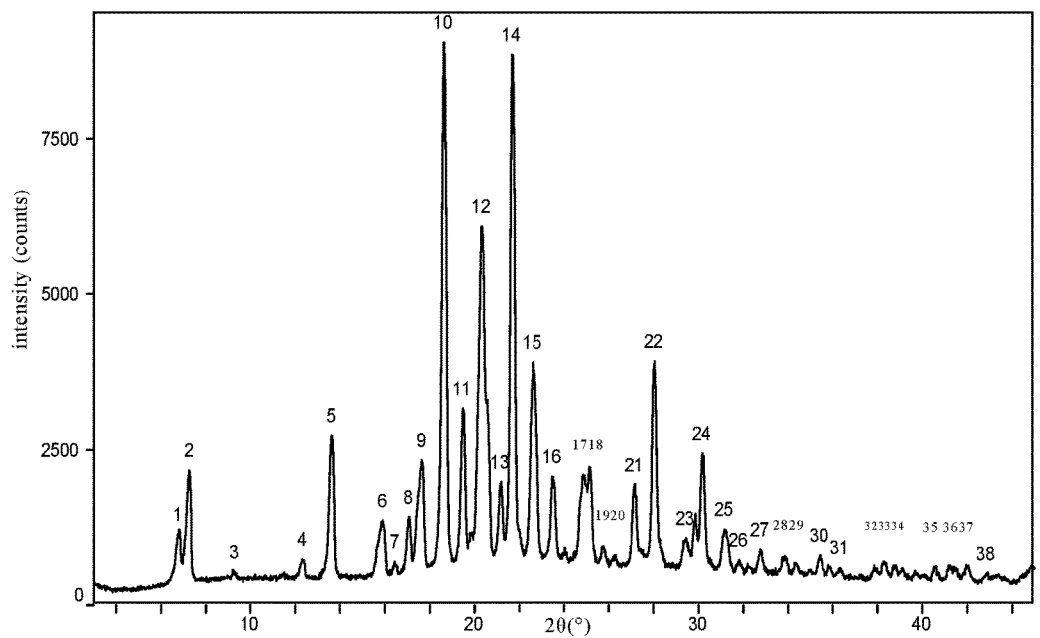
FIG. 5a shows an X-ray powder diffraction pattern of polymorph V.
Figure 5B:
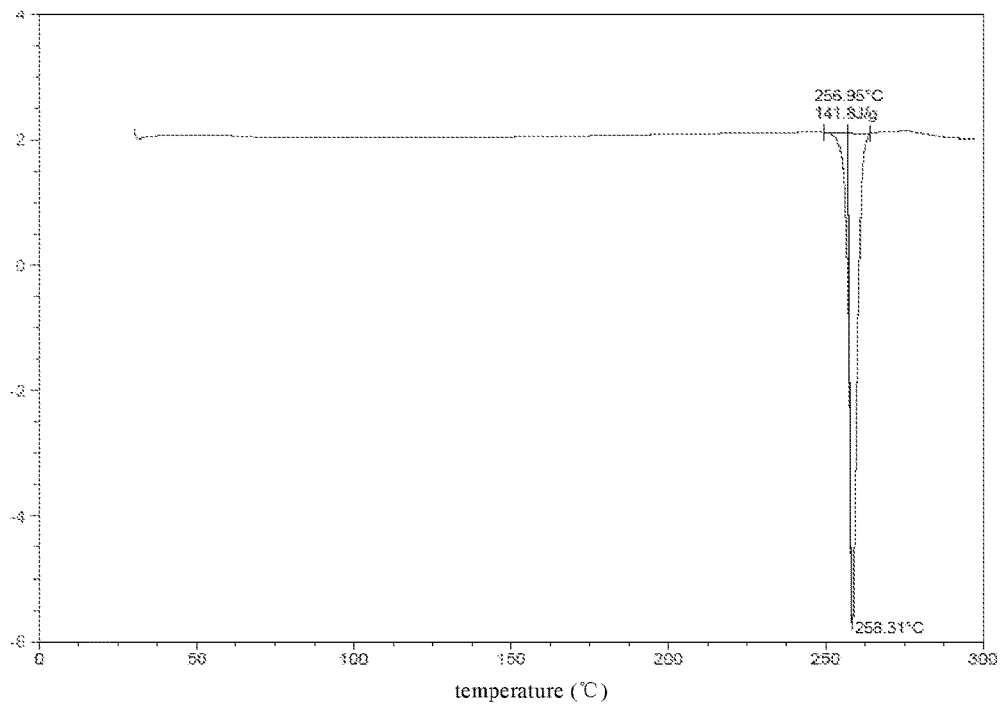
FIG. 5b shows a differential scanning calorimetry pattern of polymorph V.

In another preferred embodiment, the polymorph V has a DSC pattern as essentially shown in FIG. 5b.

(6) Polymorph VI

The polymorph VI has a maximum peak at 259.38° C.±2° C. (or ±1° C., or ±0.5° C.) in DSC pattern.

Figure 6A:
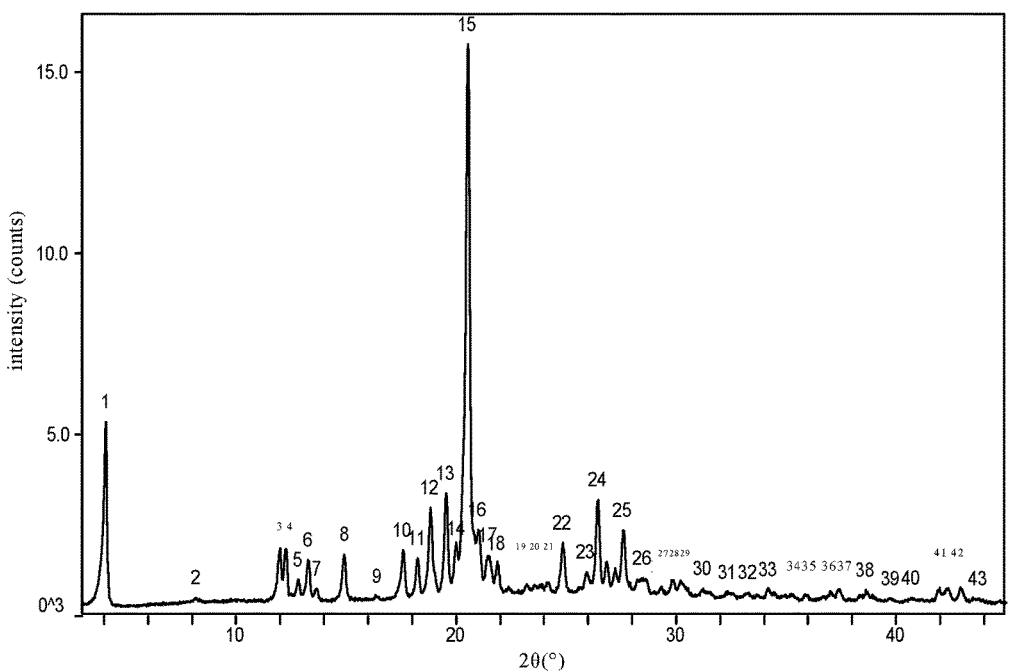
FIG. 6a shows an X-ray powder diffraction pattern of polymorph VI.
Figure 6B:
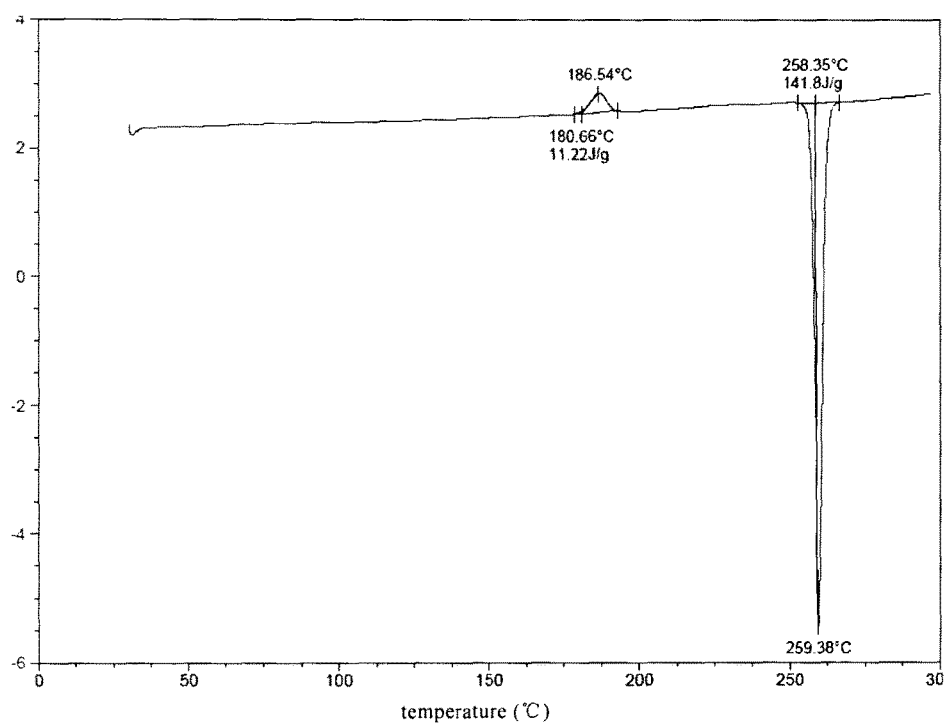
FIG. 6b shows a differential scanning calorimetry pattern of polymorph VI.

In another preferred embodiment, polymorph VI has a DSC pattern as essentially shown in FIG. 6b.

Nuclear magnetic resonance (NMR) may also be used to aid in the determination of the crystal structure. The detecting methods are known in the art, The present invention preferably uses Bruker Avance III plus-400 MHz.

Active Ingredients

As used herein, the term "active ingredients" or "active compound" refers to the polymorphs of the present invention, i.e. polymorphs of compound I or pharmaceutically acceptable salts thereof (such as the hydrochloride), or solvates thereof.

Pharmaceutical Composition and the Method of Administration

The polymorphs of the present invention possess outstanding inhibitory activity against non-receptor tyrosine kinase, such as JAK kinases. Therefore, the polymorphs of the present invention and the pharmaceutical composition including polymorphs of the present invention as main active ingredients can be used for treating, preventing and alleviating diseases mediated by non-receptor tyrosine kinase (e.g. JAK kinases). Based on the prior art, the polymorphs of the present invention can treat the following diseases: cancer, myeloproliferative and inflammatory diseases etc.

The pharmaceutical composition of the present invention comprises the polymorphs of the present invention and pharmaceutically acceptable excipients or carriers in a safe and effective dosage range.

Wherein, the term "safe and effective dosage" refers to the amount of the compounds (or the polymorphs) which is enough to improve the patient's condition without any serious side effect. Generally, the pharmaceutical composition contains 1-2000 mg polymorphs of the invention per dose, preferably, 10-200 mg polymorphs of the invention per dose. Preferably, "per dose" means one capsule or tablet.

"Pharmaceutically acceptable carrier" means one or more compatible solid or liquid fillers or gel materials, which are suitable for human, and must have sufficient purity and sufficiently low toxicity. "Compatibility" herein means that the components of the compositions can be blended with the compounds of the invention or with each other, and would not significantly reduce the efficacy of the compounds. Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc), emulsifiers (such as Tween®), wetting agent (such as sodium dodecyl sulfate), coloring agents, flavoring agents, stabilizers, antioxidants, preservatives, pyrogen-free water, etc.

There is no special limitation of administration mode for the polymorphs or pharmaceutical compositions of the present invention, and the representative administration mode includes (but is not limited to): oral, intratumoral, rectal, parenteral (intravenous, intramuscular or subcutaneous), and topical administration.

Solid dosage forms for oral administration include capsules, tablets, pills, powders and granules. In these solid dosage forms, the active ingredients are mixed with at least one conventional inert excipient (or carrier), such as sodium citrate or $CaHPO_4$, or mixed with any of the following components: (a) fillers or compatibilizer, for example, starch, lactose, sucrose, glucose, mannitol and silicic acid; (b) binders, for example, hydroxymethyl cellulose, alginates, gelatin, polyvinylpyrrolidone, sucrose and arabic gum; (c) humectant, such as, glycerol; (d) disintegrating agents such as agar, calcium carbonate, potato starch or tapioca starch, alginic acid, certain composite silicates, and sodium carbonate; (e) dissolution-retarding agents, such as paraffin; (f) absorption accelerators, for example, quaternary ammonium compounds; (g) wetting agents, such as cetyl alcohol and glyceryl monostearate; (h) adsorbents, for example, kaolin; and (i) lubricants such as talc, stearin calcium, magnesium stearate, solid polyethylene glycol, sodium lauryl sulfate, or the mixtures thereof. In capsules, tablets and pills, the dosage forms may also contain buffering agents.

The solid dosage forms such as tablets, sugar pills, capsules, pills and granules can be prepared by using coating and shell materials, such as enteric coatings and any other materials known in the art. They can contain a opaque agent. The release of the active compounds or compounds in the compositions can be released in a delayed mode in a given portion of the digestive tract. Examples of the embedding components include polymers and waxes. If necessary, the active compounds and one or more above excipients can form microcapsules.

Liquid dosage forms for oral administration include pharmaceutically acceptable emulsions, solutions, suspensions, syrups or tinctures. In addition to the active ingredients, the liquid dosage forms may contain any conventional inert diluents known in the art such as water or other solvents, solubilizers and emulsifiers, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the combination thereof.

Besides these inert diluents, the composition may also contain additives such as wetting agents, emulsifiers, and suspending agent, sweetener, flavoring agents and perfume.

In addition to the active ingredients, the suspension may contain suspending agent, for example, ethoxylated isooctadecanol, polyoxyethylene sorbitol and sorbitan esters, microcrystalline cellulose, methanol aluminum and agar, or the combination thereof.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

The dosage forms for topical administration of compounds of the invention include ointments, powders, patches, aerosol, and inhalants. The active ingredients are mixed with physiologically acceptable carriers and any preservatives, buffers, or propellant if necessary, under sterile conditions.

Polymorphs of the present invention can be administrated alone, or in combination with any other pharmaceutically acceptable compounds.

When the pharmaceutical compositions are used, a safe and effective amount of polymorph of the present invention is applied to a mammal (such as human) in need of, wherein the dose of administration is a pharmaceutically effective dose. For a person weighed 60 kg, the daily dose is usually 1-2000 mg, preferably 20-500 mg. Of course, the particular dose should also depend on various factors, such as the route of administration, patient healthy status, which are well within the skills of an experienced physician.

The main advantages of the present invention include:
1. a series of novel polymorphs of N-(cyanomethyl)-4-(2-((4-(2',2',6',6'-$d_4$-morpholino)phenyl)amino)pyrimidin-4-yl)benzamide or pharmacologically acceptable salts thereof, or solvates thereof are provided. The polymorphs of the present invention comprise polymorphs I to VI.
2. Uses of various polymorphs are provided, for preparing a pharmaceutical composition useful for inhibiting non-receptor tyrosine kinase (such as JAK kinase), thereby for treating cancer, myeloproliferative and inflammatory diseases.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacture's instructions. Unless indicated otherwise, parts and percentage are calculated by weight. Unless indicated otherwise, all quantities including quantities, percentages, fractions and ratios are to be understood as modified by the word "about" and amounts are not intended to denote significant digits.

EXAMPLE 1 PREPARATION OF POLYMORPH I OF N-(CYANOMETHYL)-4-(2-((4-(2',2',6',6'-D$_4$-MORPHOLINO)PHENYL)AMINO)PYRIMIDIN-4-YL)BENZAMIDE DIHYDROCHLORIDE 500 mg of N-(cyanomethyl)-4-(2-((4-(2',2',6',6'-$d_4$-morpholino)phenyl)amino)pyrimidin-4-yl)benzamide was added to 5.0 ml of anhydrous ethanol, stirred at room temperature in suspension. 2.3 ml of freshly prepared hydrochloric acid solution in ethanol (concentration of hydrogen chloride is 40 mg/ml) was added dropwise at room temperature, and after addition the suspended mixture was stirred for another 2.5 h at room temperature. The mixture was filtered, and washed with anhydrous ethanol, the solid was dried under high vacuum for 6 h at 40±5° C. to give a yellow solid.

The sample was identified as the title crystalline compound by $^1$H NMR, X-ray powder diffraction, DSC, etc., with a weight of 512 mg and a yield of 87%.

$^1$H NMR (400 MHz, DMSO-$d_6$) δ 10.15 (s, 1H), 9.59 (t, J=4.0 Hz, 1H), 8.66 (d, J=4.0 Hz, 1H), 8.30 (d, J=8.0 Hz, 2H), 8.09 (d, J=8.0 Hz, 2H), 7.98 (d, J=8.0 Hz, 2H), 7.85 (d, J=8.0 Hz, 2H), 7.59 (d, J=4.0 Hz, 1H), 4.36 (d, J=4.0 Hz, 2H), 4.10 (s, 4H).

Elemental analysis: C: 55.89% H: 5.79% N: 16.74%.

Figure 1C:
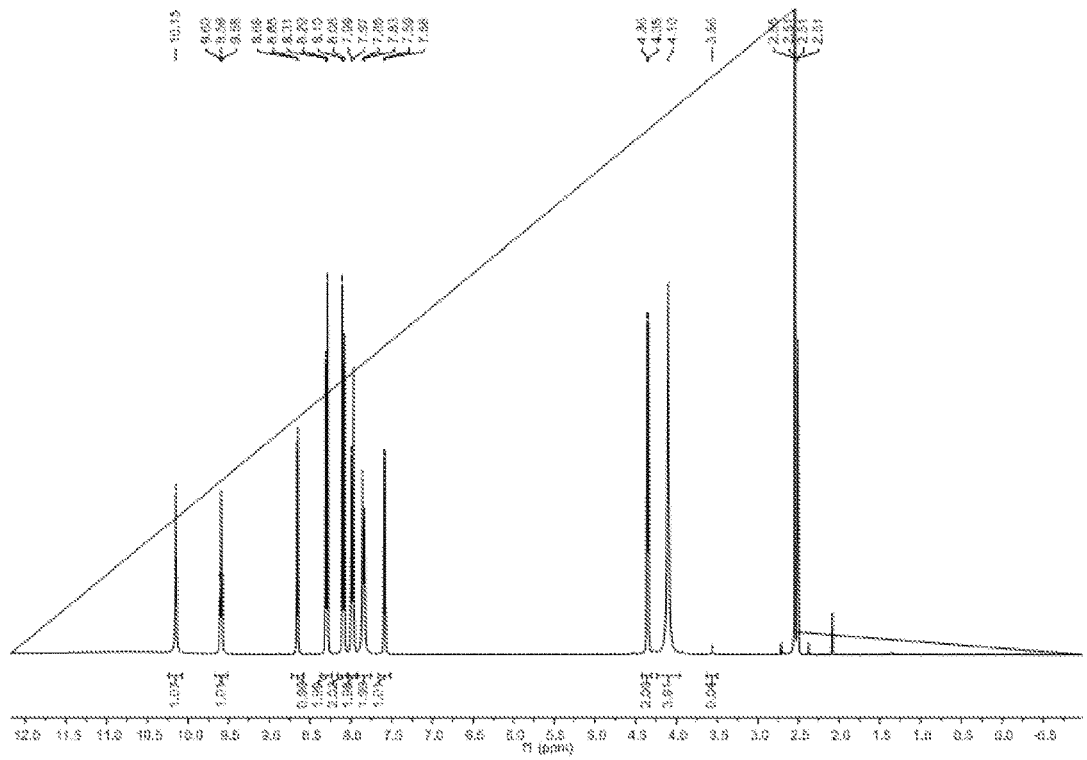
FIG. 1c shows a $^1$H NMR pattern of polymorph I.

The X-ray powder diffraction pattern is shown in FIG. a and parameters of each peak are shown in Table 1, the differential scanning calorimetry pattern (DSC) is shown in FIG. 1b, and ¹H NMR pattern is shown in FIG. 1c.

TABLE 1

| Peak No. | 2θ(°) | Height | relative intensity (I %) |
|---|---|---|---|
| 1 | 5.426 | 1014 | 51.3 |
| 2 | 8.827 | 518 | 26.2 |
| 3 | 9.985 | 1835 | 92.9 |
| 4 | 12.870 | 408 | 20.7 |
| 5 | 13.424 | 939 | 47.5 |
| 6 | 14.765 | 1417 | 71.7 |
| 7 | 15.537 | 815 | 41.3 |
| 8 | 16.462 | 644 | 32.6 |
| 9 | 17.193 | 854 | 43.2 |
| 10 | 17.923 | 722 | 36.6 |
| 11 | 18.122 | 731 | 37.0 |
| 12 | 19.268 | 848 | 42.9 |
| 13 | 20.862 | 755 | 38.2 |
| 14 | 21.127 | 647 | 32.8 |
| 15 | 22.019 | 495 | 25.1 |
| 16 | 22.896 | 730 | 37.0 |
| 17 | 23.253 | 522 | 26.4 |
| 18 | 25.148 | 1975 | 100.0 |
| 19 | 26.217 | 753 | 38.1 |
| 20 | 26.566 | 1358 | 68.8 |
| 21 | 27.098 | 762 | 38.6 |
| 22 | 28.094 | 568 | 28.8 |
| 23 | 28.485 | 527 | 26.7 |
| 24 | 28.940 | 476 | 24.1 |
| 25 | 29.529 | 642 | 32.5 |
| 26 | 29.745 | 615 | 31.1 |
| 27 | 30.282 | 794 | 40.2 |
| 28 | 31.206 | 435 | 22.0 |
| 29 | 31.925 | 399 | 20.2 |
| 30 | 34.184 | 397 | 20.1 |
| 31 | 37.841 | 277 | 14.0 |
| 32 | 39.225 | 280 | 14.2 |
| 33 | 40.784 | 329 | 16.7 |
| 34 | 41.111 | 297 | 15.0 |
| 35 | 41.111 | 297 | 15.0 |

EXAMPLE 2 PREPARATION OF POLYMORPH I OF N-(cyanomethyl)-4-(2-((4-(2',2',6',6'-D$_4$-MORPHOLINO)PHENYL)AMINO)PYRIMIDIN-4-yl)BENZAMIDE DIHYDROCHLORIDE 1.0 g of N-(cyanomethyl)-4-(2-((4-(2',2',6',6'-d$_4$-morpholino)phenyl)amino)pyrimidin-4-yl)benzamide was added to 4.0 ml of glacial acetic acid, stirred at room temperature until totally dissolved, then 5.2 ml of freshly prepared hydrochloric acid solution in ethanol (concentration of hydrogen chloride is 40 mg/ml) was added dropwise at room temperature. After addition the mixture was stirred for another 2.5 h, a solid was crystallized, filtered, and washed with anhydrous ethanol, and the solid was dried for 6 h under high vacuum at 55±5° C. to give a yellow solid, which is the title crystalline compound, with a weight of 1.1 g and a yield of 94%. The X-ray powder diffraction pattern is the same as that shown in FIG. 1a.

EXAMPLE 3 PREPARATION OF POLYMORPH I OF N-(CYANOMETHYL)-4-(2-((4-(2',2',6',6'-D$_4$-MORPHOLINO)PHENYL)AMINO)PYRIMIDIN-4-YL)BENZAMIDE DIHYDROCHLORIDE 1.0 g of N-(cyanomethyl)-4-(2-((4-(2',2',6',6'-d$_4$-morpholino)phenyl)amino)pyrimidin-4-yl)benzamide was added to 40 ml of absolute methanol, and stirred at room temperature, then 4.8 ml of freshly prepared hydrochloric acid solution in ethanol (concentration of hydrogen chloride is 40 mg/ml) was added dropwise. After addition, the mixture was filtered, the filtrate was stirred at room temperature for another 2 h. The solid was crystallized, filtered, rinsed with absolute methanol, and dried for 6 h under high vacuum at 55±5° C. to give a yellow solid, which is the title crystalline compound, with a weight of 0.88 g and a yield of 75%. The X-ray powder diffraction pattern is the same as that shown in FIG. 1a.

EXAMPLE 4 PREPARATION OF POLYMORPH I OF N-(CYANOMETHYL)-4-(2-((4-(2',2',6',6'-D$_4$-MORPHOLINO)PHENYL)AMINO)PYRIMIDIN-4-YL)BENZAMIDE DIHYDROCHLORIDE 500 mg of N-(cyanomethyl)-4-(2-((4-(2',2',6',6'-d$_4$-morpholino)phenyl)amino)pyrimidin-4-yl)benzamide was suspended and stirred in 5.0 ml of absolute methanol, slightly over 2 equivalents of concentrated hydrochloric acid was added. The mixture was slowly dissolved under stirring, soon the solid was crystallized, then 50 mg of purified water was supplemented and the stirring was continued for 16 hours. The mixture was filtered and dried to give a yellow solid, which is the title crystalline compound with a weight of 420 mg and a yield of 72%. The X-ray powder diffraction pattern is the same as that shown in FIG. 1a.

EXAMPLE 5 PREPARATION OF POLYMORPH II OF N-(CYANOMETHYL)-4-(2-((4-(2',2',6',6'-D$_4$-MORPHOLINO)PHENYL)AMINO)PYRIMIDIN-4-YL)BENZAMIDE DIHYDROCHLORIDE MONOHYDRATE 109 ml of dimethylsulfoxide was added to 34.0 g of N-(cyanomethyl)-4-(2-((4-(2',2',6',6'-d$_4$-morpholino)phenyl)amino)pyrimidin-4-yl)benzamide, which was stirred at room temperature until totally dissolved. 177 ml of freshly prepared hydrochloric acid solution in ethanol (concentration of hydrogen chloride is 40 mg/ml) was added dropwise at room temperature, and after addition the mixture was stirred was for another 2 h at room temperature, the solid was crystallized, filtered, washed with anhydrous ethanol, and dried for 6 h under high vacuum at 55±5° C. to give a yellow solid.

The sample was identified as the title crystalline compound by ¹H NMR, X-ray powder diffraction, DSC, etc., with a weight of 38.1 g and a yield of 92%.

¹H NMR (400 MHz, DMSO-d$_6$) δ 10.12 (s, 1H), 9.55 (t, J=4.0 Hz, 1H), 8.66 (d, J=4.0 Hz, 1H), 8.30 (d, J=8.0 Hz, 2H), 8.09 (d, J=8.0 Hz, 2H), 7.98 (d, J=8.0 Hz, 2H), 7.82 (d, J=8.0 Hz, 2H), 7.58 (d, J=8.0 Hz, 1H), 7.0 (brs, 3H), 4.36 (d, J=8.0 Hz, 2H), 4.09 (s, 4H).

Elemental analysis: C: 54.77% H: 4.64% N: 16.35%

Figure 2C:
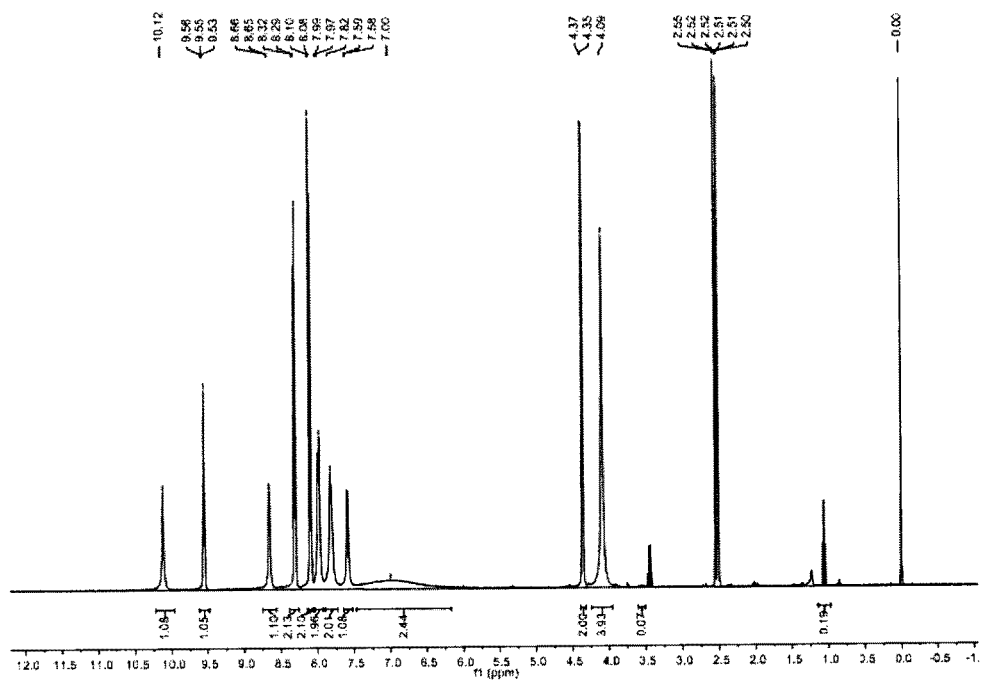
FIG. 2c shows a $^1$H NMR pattern of polymorph II.

The X-ray powder diffraction pattern is shown in FIG. 2a and parameters of each peak are shown in Table 2, the differential scanning calorimetry pattern (DSC) is shown in FIG. 2b, and ¹H NMR pattern is shown in FIG. 2c.

TABLE 2

| Peak No. | 2θ(°) | Height | relative intensity (I %) |
|---|---|---|---|
| 1 | 7.578 | 786 | 13.5 |
| 2 | 9.194 | 402 | 6.9 |
| 3 | 9.912 | 405 | 7.0 |
| 4 | 12.082 | 662 | 11.4 |
| 5 | 12.428 | 539 | 9.3 |
| 6 | 13.370 | 393 | 6.8 |
| 7 | 15.181 | 1088 | 18.7 |
| 8 | 16.642 | 877 | 15.1 |

TABLE 2-continued

| Peak No. | 2θ(°) | Height | relative intensity (I %) |
|---|---|---|---|
| 9 | 17.249 | 1953 | 33.7 |
| 10 | 17.487 | 1139 | 19.6 |
| 11 | 18.515 | 1293 | 22.3 |
| 12 | 19.224 | 1888 | 32.5 |
| 13 | 19.917 | 722 | 12.4 |
| 14 | 20.487 | 768 | 13.2 |
| 15 | 21.036 | 525 | 9.0 |
| 16 | 21.576 | 497 | 8.6 |
| 17 | 22.323 | 1374 | 23.7 |
| 18 | 22.603 | 1657 | 28.6 |
| 19 | 23.885 | 5803 | 100.0 |
| 20 | 24.575 | 1211 | 20.9 |
| 21 | 25.061 | 788 | 13.6 |
| 22 | 25.581 | 1592 | 27.4 |
| 23 | 26.624 | 867 | 14.9 |
| 24 | 27.003 | 1468 | 25.3 |
| 25 | 27.811 | 710 | 12.2 |
| 26 | 28.265 | 648 | 11.2 |
| 27 | 29.488 | 2278 | 39.3 |
| 28 | 30.201 | 864 | 14.9 |
| 29 | 31.026 | 713 | 12.3 |
| 30 | 32.133 | 690 | 11.9 |
| 31 | 32.627 | 577 | 9.9 |
| 32 | 33.422 | 497 | 8.6 |
| 33 | 34.464 | 498 | 8.6 |
| 34 | 34.957 | 569 | 9.8 |
| 35 | 36.261 | 516 | 8.9 |
| 36 | 36.644 | 476 | 8.2 |
| 37 | 37.049 | 462 | 8.0 |
| 38 | 37.505 | 468 | 8.1 |
| 39 | 38.588 | 409 | 7.0 |
| 40 | 39.537 | 524 | 9.0 |
| 41 | 40.818 | 339 | 5.8 |
| 42 | 41.709 | 597 | 10.3 |
| 43 | 44.132 | 319 | 5.5 |

EXAMPLE 6 PREPARATION OF POLYMORPH II OF N-(CYANOMETHYL)-4-(2-((4-(2',2',6',6'-D$_4$-MORPHOLINO)PHENYL)AMINO)PYRIMIDIN-4-YL)BENZAMIDE DIHYDROCHLORIDE MONOHYDRATE 302.0 g of N-(cyanomethyl)-4-(2-((4-(2',2',6',6'-d$_4$-morpholino)phenyl)amino)pyrimidin-4-yl)benzamide dihydrochloride (polymorph I) sample was finely ground and stored in an environment with humidity of more than 90% for 4 days to give a yellow solid.

The sample was identified as the title crystalline compound by $^1$H NMR, X-ray powder diffraction, DSC, etc., with a weight of 312 g and a yield of 99.7%. The X-ray powder diffraction pattern is the same as that shown in FIG. 2a.

EXAMPLE 7 PREPARATION OF POLYMORPH II OF N-(CYANOMETHYL)-4-(2-((4-(2',2',6',6'-D$_4$-MORPHOLINO)PHENYL)AMINO)PYRIMIDIN-4-YL)BENZAMIDE DIHYDROCHLORIDE MONOHYDRATE 3.15 L of dimethylsulfoxide was added to 880 g of N-(cyanomethyl)-4-(2-((4-(2',2',6',6'-d$_4$-morpholino)phenyl)amino)pyrimidin-4-yl)benzamide, which was stirred at 35° C. until totally dissolved. 4.14 L of freshly prepared hydrochloric acid solution in ethanol (concentration of hydrogen chloride is 40 mg/ml) was added at room temperature, and then 25 g of polymorph II seed crystal was added. The mixture was stirred for another 2 h at room temperature, the solid was crystallized, filtered, rinsed with acetone, and dried for 6 h under high vacuum at 55±5° C. to give a yellow solid.

The sample was identified as the title crystalline compound by X-ray powder diffraction, DSC, etc., with a weight of 885.0 g and a yield of 82%. The X-ray powder diffraction pattern is the same as that shown in FIG. 2a.

EXAMPLE 8 PREPARATION OF POLYMORPH II OF N-(CYANOMETHYL)-4-(2-((4-(2',2',6',6'-D$_4$-MORPHOLINO)PHENYL)AMINO)PYRIMIDIN-4-YL)BENZAMIDE DIHYDROCHLORIDE MONOHYDRATE 10 ml of acetone and 0.5 ml of purified water were added to 1.0 g of N-(cyanomethyl)-4-(2-((4-(2',2',6',6'-d$_4$-morpholino)phenyl)amino)pyrimidin-4-yl)benzamide dihydrochloride (polymorph I) sample, which was stirred at room temperature for 3 h. The mixture was filtered, rinsed with acetone, and dried for 3 h under high vacuum at room temperature to give a yellow solid, which is the title crystalline compound, with a weight of 950 mg and a yield of 92%.

The sample was identified as the title crystalline compound by $^1$H NMR, X-ray powder diffraction, DSC, etc., The X-ray powder diffraction pattern is the same that shown as in FIG. 2a.

EXAMPLE 9 PREPARATION OF POLYMORPH II OF N-(CYANOMETHYL)-4-(2-((4-(2',2',6',6'-D$_4$-MORPHOLINO)PHENYL)AMINO)PYRIMIDIN-4-YL)BENZAMIDE DIHYDROCHLORIDE MONOHYDRATE

N-(cyanomethyl)-4-(2-((4-(2',2',6',6'-d$_4$-morpholino)phenyl)amino)pyrimidin-4-yl)benzamide (2.0 g) and dimethyl sulfoxide (5 ml) were added into a four-necked flask, which were stirred at room temperature until totally dissolved. 10 mL of freshly prepared hydrochloric acid solution in ethanol (concentration of hydrogen chloride is 40 mg/ml) was slowly dropwise added at room temperature. After addition, the mixture was stirred for another 5 h, and then filtered. The filter cake is quickly rinsed with absolute methanol, dried for 6 h under high vacuum at 55±5° C. to give a yellow solid, which is the title crystalline compound, with a weight of 1.92 g and a yield of 79%. The X-ray powder diffraction pattern is the same as that shown in FIG. 2a.

EXAMPLE 10 PREPARATION OF POLYMORPH II OF N-(CYANOMETHYL)-4-(2-((4-(2',2',6',6'-D$_4$-MORPHOLINO)PHENYL)AMINO)PYRIMIDIN-4-YL)BENZAMIDE DIHYDROCHLORIDE MONOHYDRATE 500 mg of N-(cyanomethyl)-4-(2-((4-(2',2',6',6'-d$_4$-morpholino)phenyl)amino)pyrimidin-4-yl)benzamide dihydrochloride solid (polymorph I) was suspended and stirred in 3.0 ml of absolute methanol, then 0.25 ml 1M of diluted hydrochloric acid was slowly added. The mixture was stirred overnight at room temperature, and filtered. The solid was washed with absolute methanol (0.5 ml×2) and 1M of diluted hydrochloric acid (0.5 ml), and dried for 8 h under high vacuum at 55±5° C. to give a solid, which is the title crystalline compound, with a weight of 326 mg and a yield of 63%. The X-ray powder diffraction pattern is the same as that shown in FIG. 2a.

EXAMPLE 11 PREPARATION OF POLYMORPH II OF N-(CYANOMETHYL)-4-(2-((4-(2',2',6',6'-D$_4$-MORPHOLINO)PHENYL)AMINO)PYRIMIDIN-4-YL)BENZAMIDE DIHYDROCHLORIDE MONOHYDRATE 500 mg of N-(cyanomethyl)-4-(2-((4-(2',2',6',6'-d$_4$-morpholino)phenyl)amino)pyrimidin-4-yl)benzamide solid was suspended and stirred in 5.0 ml of absolute methanol, slightly over 2 equivalents of concentrated hydrochloric acid (0.21 ml) was added. The mixture was stirred until totally dissolved, then 20 mg of N-(cyanomethyl)-4-(2-((4-(2',2',6',6'-$d_4$-morpholino)phenyl)amino)pyrimidin-4-yl)benzamide dihydrochloride monohydrate seed crystals (polymorph II) was immediately added, and 50 mg of purified water was further supplemented. The mixture was stirred at room temperature for 4 h, and filtered. The solid was washed with absolute methanol and 1M of diluted hydrochloric acid (0.5 ml), and dried to give a solid which is the title crystalline compound, with a weight of 462 mg and a yield of 76%. The X-ray powder diffraction pattern is the same as that shown in FIG. 2a.

EXAMPLE 12 PREPARATION OF POLYMORPH II OF N-(CYANOMETHYL)-4-(2-((4-(2',2',6',6'-D$_4$-MORPHOLINO)PHENYL)AMINO)PYRIMIDIN-4-YL)BENZAMIDE DIHYDROCHLORIDE MONOHYDRATE 1.465 kg of N-(cyanomethyl)-4-(2-((4-(2',2',6',6'-$d_4$-morpholino)phenyl)amino)pyrimidin-4-yl)benzamide and 5.640 kg of dimethylsulfoxide were added into 20 L of reactor. The mixture was stirred at a temperature controlled at about 40 degrees until totally dissolved, and filtered. Mother liquor was transferred into a reactor, and 5.515 kg of freshly prepared hydrochloric acid solution in acetone (0.765 kg of hydrochloric acid was added to 4.750 kg of acetone) was added one-time. The mixture was stirred at room temperature for 4.5 h, and filtered. The solid was rinsed with acetone, and dried by suction. The solid is smashed and then transferred into a reactor, and acetone (9.240 kg) and water (0.735 kg) were added. The stirring was continued for 2.5 h at room temperature, and the mixture was filtered. The solid was rinsed with acetone, dried under high vacuum at 55±5° C. to give a yellow solid, with a weight of 1.470 kg and a yield of 82%. The X-ray powder diffraction pattern is the same as that shown in FIG. 2a.

EXAMPLE 13 POLYMORPH III OF N-(CYANOMETHYL)-4-(2-((4-(2',2',6',6'-D$_4$-MORPHOLINO)PHENYL)AMINO)PYRIMIDIN-4-YL) BENZAMIDE MONOHYDROCHLORIDE 1 ml of N-methylpyrrolidone was added to 300 mg of N-(cyanomethyl)-4-(2-((4-(2',2',6',6'-$d_4$-morpholino)phenyl)amino)pyrimidin-4-yl)benzamide, after the mixture was totally dissolved, 4.0 ml of anhydrous ethanol was added. The mixture was stirred, and 1.0 ml of freshly prepared hydrochloric acid solution in ethanol (concentration of hydrogen chloride is 40 mg/ml) was slowly dropwise added at room temperature. After addition the mixture was stirred for 2 minutes and totally dissolved. The stirring was continued for 3 h. The solid was crystallized, filtered, rinsed with anhydrous ethanol, and dried under high vacuum at room temperature for 6 h to give a greyish white solid.

The sample was identified as the title crystalline compound by $^1$H NMR, X-ray powder diffraction, DSC, etc., with a weight of 285 mg and a yield of 87%.

$^1$H NMR (400 MHz, DMSO-$d_6$) δ 10.05 (s, 1H), 9.54 (1, J=4.0 Hz, 1H), 8.64 (d, J=4.0 Hz, 1H), 8.29 (d, J=8.0 Hz, 2H), 8.08 (d, J=8.0 Hz, 2H), 7.95 (d, J=8.0 Hz, 2H), 7.72-7.55 (m, 3H), 4.37 (d, J=4.0 Hz, 2H), 4.05 (s, 4H).

Elemental analysis: C: 60.42% H: 6.23% N: 17.90%

Figure 3C:
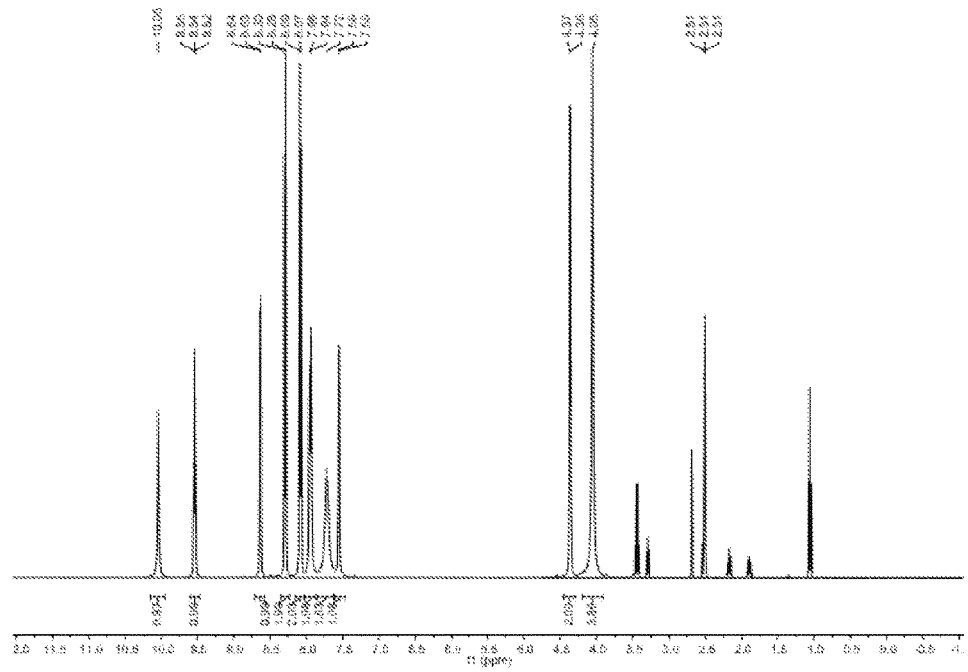
FIG. 3c shows a $^1$H NMR pattern of polymorph III.

The X-ray powder diffraction pattern is shown in FIG. 3a and parameters of each peak are shown in Table 3, the differential scanning calorimetry pattern (DSC) is shown in FIG. 3b, and $^1$H NMR pattern is shown in FIG. 3c,

TABLE 3

| Peak No. | 2θ(°) | Height | relative intensity (I %) |
|---|---|---|---|
| 1 | 4.400 | 677 | 9.3 |
| 2 | 8.843 | 841 | 11.6 |
| 3 | 9.252 | 836 | 11.5 |
| 4 | 10.244 | 571 | 7.9 |
| 5 | 11.963 | 754 | 10.4 |
| 6 | 12.530 | 801 | 11.0 |
| 7 | 13.305 | 1732 | 23.8 |
| 8 | 14.014 | 816 | 11.2 |
| 9 | 15.178 | 5422 | 74.6 |
| 10 | 16.204 | 2084 | 28.7 |
| 11 | 16.953 | 1762 | 24.2 |
| 12 | 17.963 | 1108 | 15.2 |
| 13 | 18.809 | 2148 | 29.6 |
| 14 | 19.090 | 997 | 13.7 |
| 15 | 20.073 | 2053 | 28.3 |
| 16 | 20.705 | 7266 | 100.0 |
| 17 | 21.733 | 1147 | 15.8 |
| 18 | 22.187 | 1296 | 17.8 |
| 19 | 22.937 | 2133 | 29.4 |
| 20 | 23.926 | 1341 | 18.5 |
| 21 | 25.958 | 1778 | 24.5 |
| 22 | 26.390 | 2908 | 40.0 |
| 23 | 27.061 | 1086 | 14.9 |
| 24 | 28.088 | 2294 | 31.6 |
| 25 | 30.280 | 967 | 13.3 |
| 26 | 31.127 | 891 | 12.3 |
| 27 | 31.837 | 1020 | 14.0 |
| 28 | 32.843 | 866 | 11.9 |
| 29 | 34.581 | 660 | 9.1 |
| 30 | 37.330 | 562 | 7.7 |
| 31 | 38.235 | 449 | 6.2 |
| 32 | 41.843 | 504 | 6.9 |

EXAMPLE 14 POLYMORPH III OF N-(CYANOMETHYL)-4-(2-((4-(2',2',6',6'-D$_4$-MORPHOLINO)PHENYL)AMINO)PYRIMIDIN-4-YL) BENZAMIDE MONOHYDROCHLORIDE 150 mg of N-(cyanomethyl)-4-(2-((4-(2',2',6',6'-$d_4$-morpholino)phenyl)amino)pyrimidin-4-yl)benzamide dihydrochloride monohydrate (polymorph II) was suspended in 6 ml of absolute methanol, and stirred at room temperature for 24 h. The mixture was filtered, and the solid was washed with absolute methanol and dried under high vacuum at 55±5° C. for 6 h to give a greyish white solid, which was the title crystalline compound, with a weight of 130 mg and a yield of 97%. The X-ray powder diffraction pattern is the same as that shown in FIG. 3a.

EXAMPLE 15 POLYMORPH III OF N-(CYANOMETHYL)-4-(2-((4-(2',2',6',6'-D$_4$-MORPHOLINO)PHENYL)AMINO)PYRIMIDIN-4-YL) BENZAMIDE MONOHYDROCHLORIDE 500 mg of N-(cyanomethyl)-4-(2-((4-(2',2',6',6'-$d_4$-morpholino)phenyl)amino)pyrimidin-4-yl)benzamide solid was suspended in 5 ml of absolute methanol, and 1 equivalent of concentrated hydrochloric acid (100 µl) was added. The mixture was stirred at room temperature for 14 h, and filtered. The solid was washed with absolute methanol, and dried to give a solid, which was the title crystalline compound, with a weight of 412 mg and a yield of 76%. The X-ray powder diffraction pattern is the same as that shown in FIG. 3a.

EXAMPLE 16 POLYMORPH IV OF N-(cyanomethyl)-4-(2-((4-(2',2',6',6'-D$_4$-MORPHOLINO)PHENYL)AMINO)PYRIMIDIN-4-YL)BENZAMIDE HYDROCHLORIDE 2 ml of purified water was added to 200 mg of N-(cyanomethyl)-4-(2-((4-(2',2',6',6'-d$_4$-morpholino)phenyl)amino)pyrimidin-4-yl)benzamide dihydrochloride (polymorph I). The mixture was stirred at room temperature for 12 h, crystallized, and filtered. The solid was washed with acetone and dried under high vacuum at room temperature for 6 h to give a greyish white solid.

The sample was identified as the title crystalline compound by $^1$H NMR, X-ray powder diffraction, DSC, etc., with a weight of 156 mg and a yield of 84%.

$^1$H NMR (400 MHz, DMSO-d$_6$) δ 10.0 (s, 1H), 9.49 (t, J=4.0 Hz, 1H), 8.64 (d, J=4.0 Hz, 1H), 8.30 (d, J=8.0 Hz, 2H), 8.07 (d, J=8.0 Hz, 2H), 7.92 (d J=8.0 Hz, 2H), 7.63-7.54 (m, 3H), 4.37 (d, J=4.0 MHz, 2H), 4.01 (s, 4H).

Elemental analysis: C: 60.96% H: 6.04% N: 18.36%.

Figure 4C:
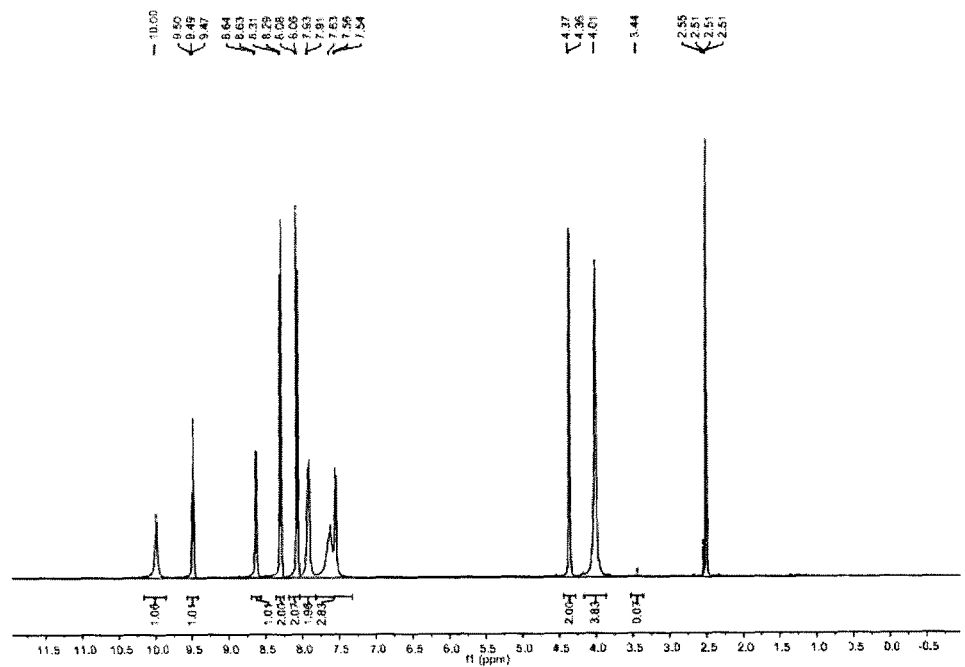
FIG. 4c shows a $^1$H NMR pattern of polymorph IV.

The X-ray powder diffraction pattern is shown in FIG. 4a and parameters of each peak are shown in Table 4, the differential scanning calorimetry pattern (DSC) is shown in FIG. 4b, and $^1$H NMR pattern is shown in FIG. 4c.

TABLE 4

| Peak No. | 2θ(°) | Height | relative intensity (I %) |
|---|---|---|---|
| 1 | 4.422 | 1275 | 25.8 |
| 2 | 8.902 | 360 | 7.3 |
| 3 | 12.493 | 3984 | 80.7 |
| 4 | 12.986 | 1815 | 36.8 |
| 5 | 13.779 | 839 | 17.0 |
| 6 | 14.447 | 4040 | 81.9 |
| 7 | 16.582 | 989 | 20.0 |
| 8 | 17.074 | 1937 | 39.3 |
| 9 | 17.627 | 3970 | 80.4 |
| 10 | 18.366 | 547 | 11.1 |
| 11 | 19.519 | 2907 | 58.9 |
| 12 | 20.586 | 584 | 11.8 |
| 13 | 20.984 | 642 | 13.0 |
| 14 | 21.906 | 860 | 17.4 |
| 15 | 22.344 | 1559 | 31.6 |
| 16 | 23.231 | 4935 | 100.0 |
| 17 | 23.805 | 4724 | 97.7 |
| 18 | 24.396 | 1260 | 25.5 |
| 19 | 24.831 | 4251 | 86.1 |
| 20 | 25.778 | 1213 | 24.6 |
| 21 | 26.569 | 1073 | 21.7 |
| 22 | 27.040 | 951 | 19.3 |
| 23 | 27.556 | 925 | 18.7 |
| 24 | 28.166 | 1251 | 25.3 |
| 25 | 28.738 | 1668 | 33.8 |
| 26 | 29.607 | 1295 | 26.2 |
| 27 | 30.180 | 954 | 19.3 |
| 28 | 30.747 | 638 | 12.9 |
| 29 | 31.741 | 1160 | 23.5 |
| 30 | 33.534 | 567 | 11.5 |
| 31 | 34.251 | 444 | 9.0 |
| 32 | 35.017 | 964 | 19.5 |
| 33 | 35.727 | 857 | 17.4 |
| 34 | 37.366 | 557 | 11.3 |
| 35 | 39.124 | 509 | 10.3 |
| 36 | 39.811 | 656 | 13.3 |
| 37 | 41.176 | 474 | 9.6 |
| 38 | 41.984 | 569 | 11.5 |
| 39 | 42.814 | 446 | 9.0 |
| 40 | 43.526 | 411 | 8.3 |
| 41 | 44.691 | 468 | 9.5 |

EXAMPLE 17 POLYMORPH IV OF N-(CYANOMETHYL)-4-(2-((4-(2',2',6',6'-D$_4$-MORPHOLINO)PHENYL)AMINO)PYRIMIDIN-4-YL) BENZAMIDE HYDROCHLORIDE 24.0 ml of purified water was added to 600 mg of N-(cyanomethyl)-4-(2-((4-(2',2',6',6'-d$_4$-morpholino)phenyl)amino)pyrimidin-4-yl)benzamide dihydrochloride monohydrate (polymorph II) sample. The mixture was stirred until the sample was totally dissolved and stirred at room temperature for 3 h. A white solid was precipitated, and filtered. The solid was washed with tetrahydrofuran, and dried at room temperature for 3 h to give a white solid, which was the title crystalline compound, with a weight of 478 mg and a yield of 89%. The X-ray powder diffraction pattern is the same as that shown in FIG. 4a.

EXAMPLE 18 POLYMORPH IV OF N-(CYANOMETHYL)-4-(2-((4-(2',2',6',6'-D$_4$-MORPHOLINO)PHENYL)AMINO)PYRIMIDIN-4-YL) BENZAMIDE HYDROCHLORIDE 5.0 ml of 1M hydrochloric acid was added to 1.0 g of N-(cyanomethyl)-4-(2-((4-(2',2',6',6'-d$_4$-morpholino)phenyl)amino)pyrimidin-4-yl)benzamide. The mixture was stirred overnight at room temperature, and a white solid was precipitated The mixture was filtered, washed with tetrahydrofuran, and dried under high vacuum at room temperature for 3 h to give a white solid, which was the title crystalline compound, with a weight of 0.8 g and a yield of 74%. The X-ray powder diffraction pattern is the same as that shown in FIG. 4a.

EXAMPLE 19 POLYMORPH IV OF N-(CYANOMETHYL)-4-(2-((4-(2',2',6',6'-D$_4$-MORPHOLINO)PHENYL)AMINO)PYRIMIDIN-4-YL) BENZAMIDE HYDROCHLORIDE 500 mg of N-(cyanomethyl)-4-(2-((4-(2',2',6',6'-d$_4$-morpholino)phenyl)amino)pyrimidin-4-yl)benzamide dihydrochloride monohydrate (polymorph II) sample was suspended and stirred in a mixture solution of methanol/water (3.5 ml/1.5 ml) for 14 h. The mixture was filtered. The solid was washed with absolute methanol, and dried under high vacuum at 40±5° C. to give a solid, which was the title crystalline compound, with a weight of 375 mg and a yield of 84%. The X-ray powder diffraction pattern is the same as that shown in FIG. 4a.

EXAMPLE 20 POLYMORPH V OF N-(CYANOMETHYL)-4-(2-((4-(2',2',6',6'-D$_4$-MORPHOLINO)PHENYL)AMINO)PYRIMIDIN-4-YL) BENZAMIDE

N-(cyanomethyl)-4-(2-((4-(2',2',6',6'-d$_4$-morpholino)phenyl)amino)pyrimidin-4-yl)benzamide (50.0 g) and dimethylsulfoxide (150 mL) was added into a reaction flask, and stirred for the dissolution. The above solution was slowly dropwise added to the pure water (500 mL). The mixture was stirred at room temperature for 2 h and filtered, the filter cake was rinsed with pure water (0.5 L×3), and dried by suction as fully as possible. The solid was dried under high vacuum at 70° C. for 6 h, to give a yellow solid.

The sample was identified as the title crystalline compound by $^1$H NMR, X-ray powder diffraction, DSC, etc., with a weight of 45.0 g and a yield of 90%.

¹H NMR (400 MHz, DMSO-d₆) δ 9.50 (s, 1H), 9.34 (t, J=4.0 Hz, 1H), 8.54 (d, J=4.0 Hz, 1H), 8.27 (d, J=8.0 Hz, 2H), 8.03 (d, J=8.0 Hz, 2H), 7.66 (d, J=8.0 Hz, 2H). 7.40 (d, J=8.0 Hz, 1H), 6.92 (d, J=8.0 Hz, 2H), 4.36 (d, J=8.0 Hz, 2H), 3.73 (s, 4H).

Elemental analysis: C: 66.08% H: 5.40% N: 19.91%

Figure 5C:
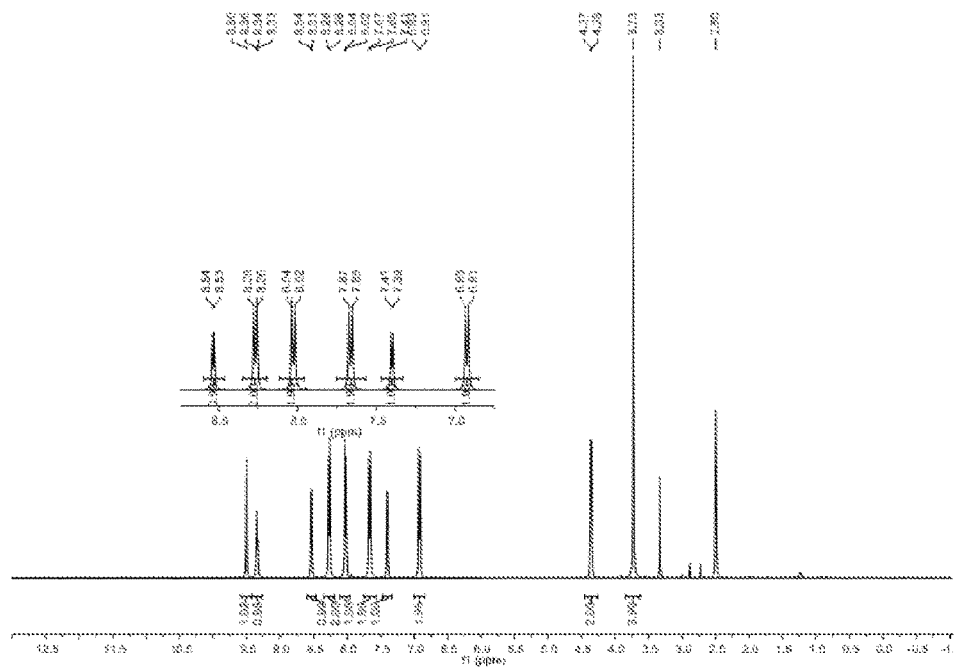
FIG. 5c shows a $^1$H NMR pattern of polymorph V.

The X-ray powder diffraction pattern is shown in FIG. 5a and parameters of each peak are shown in Table 5, the differential scanning calorimetry pattern (DSC) is shown in FIG. 5b, and ¹H NMR pattern is shown in FIG. 5c.

TABLE 5

| Peak No. | 2θ(°) | Height | relative intensity (I %) |
|---|---|---|---|
| 1 | 6.772 | 1115 | 12.3 |
| 2 | 7.263 | 2155 | 23.8 |
| 3 | 9.273 | 507 | 5.6 |
| 4 | 12.319 | 705 | 7.8 |
| 5 | 13.621 | 2708 | 29.9 |
| 6 | 15.909 | 1332 | 14.7 |
| 7 | 16.441 | 671 | 7.4 |
| 8 | 17.075 | 1392 | 15.3 |
| 9 | 17.647 | 2314 | 25.5 |
| 10 | 18.634 | 9072 | 100.0 |
| 11 | 19.483 | 3150 | 34.7 |
| 12 | 20.331 | 6091 | 67.1 |
| 13 | 21.179 | 1963 | 21.6 |
| 14 | 21.675 | 8871 | 97.8 |
| 15 | 22.621 | 3896 | 42.9 |
| 16 | 23.509 | 2055 | 22.7 |
| 17 | 24.852 | 2075 | 22.9 |
| 18 | 25.148 | 2209 | 24.3 |
| 19 | 25.759 | 924 | 10.2 |
| 20 | 26.305 | 776 | 8.6 |
| 21 | 27.179 | 1920 | 21.2 |
| 22 | 28.048 | 3915 | 43.2 |
| 23 | 29.450 | 1050 | 11.6 |
| 24 | 30.181 | 2429 | 26.8 |
| 25 | 31.168 | 1189 | 13.1 |
| 26 | 31.818 | 699 | 7.7 |
| 27 | 32.767 | 865 | 9.5 |
| 28 | 33.853 | 759 | 8.4 |
| 29 | 34.364 | 640 | 7.1 |
| 30 | 35.430 | 771 | 8.5 |
| 31 | 36.343 | 574 | 6.3 |
| 32 | 37.861 | 611 | 6.7 |
| 33 | 38.275 | 674 | 7.4 |
| 34 | 38.822 | 607 | 6.7 |
| 35 | 40.616 | 601 | 6.6 |
| 36 | 41.251 | 593 | 6.5 |
| 37 | 41.967 | 615 | 6.8 |
| 38 | 42.855 | 474 | 5.2 |

EXAMPLE 21 POLYMORPH VI OF N-(CYANOMETHYL)-4-(2-((4-(2',2',6',6'-D₄-MORPHOLINO)PHENYL)AMINO)PYRIMIDIN-4-YL)BENZAMIDE 1.5 g of N-(cyanomethyl)-4-(2-((4-(2',2',6',6'-d₄-morpholino)phenyl)amino)pyrimidin-4-yl)benzamide dihydrochloride monohydrate (polymorph II) was added to 150 ml of a pH 6.8 phosphate buffer (formulated according to the Pharmacopoeia). The mixture was magnetically stirred for 16 h and filtered. The solid was washed with pH 6.8 phosphate buffer (5.0 ml×2), dried under vacuum at 50° C. for 8 h to give a yellow solid of 1.1 g. The sample was identified as the title crystalline compound by ¹H NMR, X-ray powder diffraction, DSC, etc., with a yield of 89%.

¹H NMR (400 MHz, DMSO-d₆) δ 9.50 (s, 1H), 9.35 (t, J=4.0 Hz, 1H), 8.53 (d, J=4.0 Hz, 1H), 8.26 (d, J=8.0 Hz, 2H), 8.02 (d, J=8.0 Hz, 2H), 7.66 (d, J=8.0 Hz, 2H), 7.40 (d, J=8.0 Hz, 1H), 6.92 (d, J=8.0 Hz, 2H), 4.35 (d, J=8.0 Hz, 2H), 3.72 (s, 4H).

Elemental analysis: C: 65.63% H: 5.59% N: 20.05%

Figure 6C:
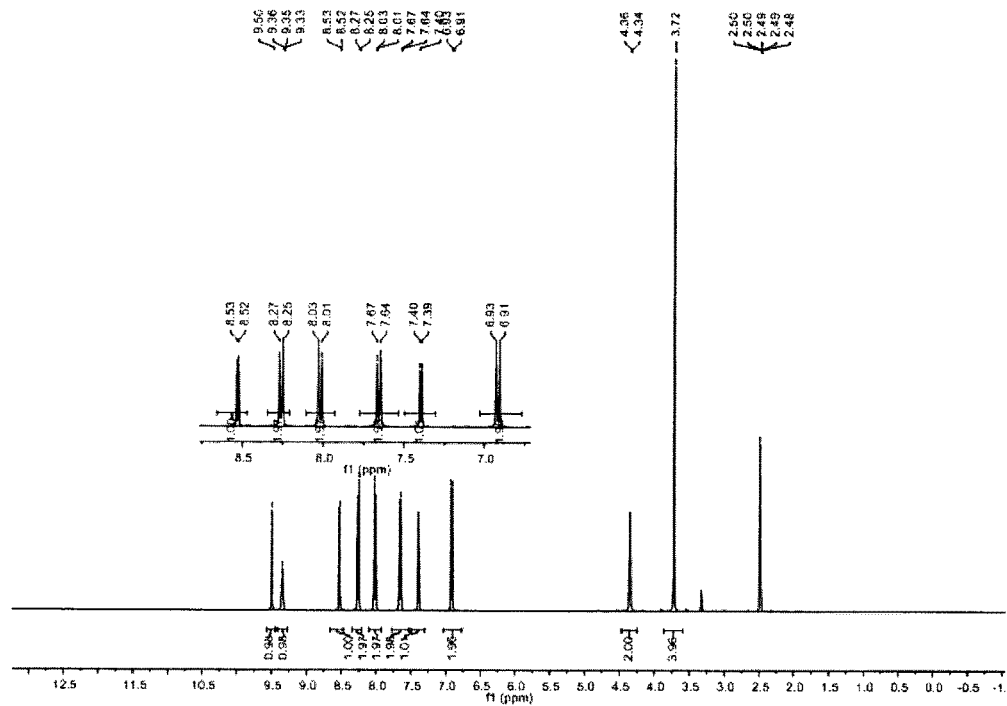
FIG. 6c shows a $^1$H NMR pattern of polymorph VI.

The X-ray powder diffraction pattern is shown in FIG. 6a and parameters of each peak are shown in Table 6, the differential scanning calorimetry pattern (DSC) is shown in FIG. 6b, and ¹H NMR pattern is shown in FIG. 6c.

TABLE 6

| Peak No. | 2θ(°) | Height | relative intensity (I %) |
|---|---|---|---|
| 1 | 4.084 | 5319 | 33.6 |
| 2 | 8.170 | 453 | 2.9 |
| 3 | 12.035 | 1578 | 10.0 |
| 4 | 12.277 | 1805 | 11.4 |
| 5 | 12.831 | 952 | 6.0 |
| 6 | 13.286 | 1500 | 9.5 |
| 7 | 13.679 | 699 | 4.4 |
| 8 | 14.922 | 1653 | 10.5 |
| 9 | 16.403 | 490 | 3.1 |
| 10 | 17.589 | 1772 | 11.2 |
| 11 | 18.257 | 1546 | 9.8 |
| 12 | 18.832 | 2951 | 18.7 |
| 13 | 19.542 | 3342 | 21.1 |
| 14 | 20.032 | 1818 | 11.5 |
| 15 | 20.529 | 15807 | 100.0 |
| 16 | 21.003 | 2332 | 14.8 |
| 17 | 21.475 | 1619 | 10.2 |
| 18 | 21.856 | 1406 | 8.9 |
| 19 | 23.231 | 829 | 5.2 |
| 20 | 23.644 | 784 | 5.0 |
| 21 | 24.200 | 961 | 6.1 |
| 22 | 24.870 | 1975 | 12.5 |
| 23 | 25.937 | 1161 | 7.3 |
| 24 | 26.468 | 3162 | 20.0 |
| 25 | 27.597 | 2320 | 14.7 |
| 26 | 28.503 | 999 | 6.3 |
| 27 | 29.349 | 766 | 4.8 |
| 28 | 29.846 | 980 | 6.2 |
| 29 | 30.237 | 898 | 5.7 |
| 30 | 31.224 | 710 | 4.5 |
| 31 | 32.366 | 600 | 3.8 |
| 32 | 33.289 | 594 | 3.8 |
| 33 | 34.202 | 678 | 4.3 |
| 34 | 35.294 | 535 | 3.4 |
| 35 | 35.885 | 546 | 3.5 |
| 36 | 37.015 | 631 | 4.0 |
| 37 | 37.426 | 744 | 4.7 |
| 38 | 38.633 | 669 | 4.2 |
| 39 | 39.786 | 430 | 2.7 |
| 40 | 40.704 | 449 | 2.8 |
| 41 | 42.378 | 713 | 4.5 |
| 42 | 42.931 | 740 | 4.7 |
| 43 | 43.744 | 434 | 2.7 |

EXAMPLE 22 STABILITY OF POLYMORPH I OF N-(CYANOMETHYL)-4-(2-((4-(2',2',6',6'-D₄-MORPHOLINO)PHENYL)AMINO)PYRIMIDIN-4-YL)BENZAMIDE DIHYDROCHLORIDE

After an accelerated test (test condition: 40±2° C., 75%±5% RH) for 6 months, the results showed that: crystal form of polymorph I was very stable; compared to freshly prepared (0 Month) polymorph I, the purity of polymorph I was almost unchanged, always above 99%, and no obvious degradated impurity was observed.

EXAMPLE 23 STABILITY OF POLYMORPH II OF N-(CYANOMETHYL)-4-(2-((4-(2',2',6',6'-D₄-MORPHOLINO)PHENYL)AMINO)PYRIMIDIN-4-YL)BENZAMIDE DIHYDROCHLORIDE MONOHYDRATE

After an accelerated test (test condition: 40±2° C., 75%±5% RH) for 6 months, the results showed that: crystal form of polymorph II was very stable; compared to freshly prepared (0 Month) polymorph II, the purity of polymorph II was almost unchanged, always above 99%, and no obvious degradated impurity was observed.

EXAMPLE 24 STABILITY OF POLYMORPH III OF N-(CYANOMETHYL)-4-(2-((4-(2',2',6',6'-D$_4$-MORPHOLINO)PHENYL)AMINO)PYRIMIDIN-4-YL)BENZAMIDE MONOHYDROCHLORIDE

After an accelerated test (test condition: 40±2° C., 75%±5% RH) for 6 months, the results showed that: crystal form of polymorph III was very stable; compared to freshly prepared (0 Month) polymorph III, the purity of polymorph III was almost unchanged, always above 99%, and no obvious degradated impurity was observed.

EXAMPLE 25 STABILITY OF POLYMORPH IV OF N-(CYANOMETHYL)-4-(2-((4-(2',2',6',6'-D$_4$-MORPHOLINO)PHENYL)AMINO)PYRIMIDIN-4-YL)BENZAMIDE HYDROCHLORIDE

After an accelerated test (test condition: 40±2° C., 75%±5% RH) for 6 months, the results showed that: crystal form of polymorph IV was very stable; compared to freshly prepared (0 Month) polymorph IV, the purity of polymorph IV was almost unchanged, always above 99%, and no obvious degradated impurity was observed.

EXAMPLE 26 STABILITY OF POLYMORPH V OF N-(CYANOMETHYL)-4-(2-((4-(2',2',6',6'-D$_4$-MORPHOLINO)PHENYL)AMINO)PYRIMIDIN-4-YL)BENZAMIDE

After an accelerated test (test condition: 40±2° C., 75%±5% RH) for 6 months, the results showed that: crystal form of polymorph V was very stable; compared to freshly prepared (0 Month) polymorph V, the purity of polymorph V was almost unchanged, always above 99%, and no obvious degradated impurity was observed.

EXAMPLE 27 STABILITY OF POLYMORPH VI OF N-(CYANOMETHYL)-4-(2-((4-(2',2',6',6'-D$_4$-MORPHOLINO)PHENYL)AMINO)PYRIMIDIN-4-YL)BENZAMIDE

After an accelerated test (test condition: 40±2° C., 75%±5% RH) for 6 months, the results showed that: crystal form of polymorph VI was very stable; compared to freshly prepared (0 Month) polymorph VI, the purity of polymorph VI was almost unchanged, always above 99%, and no obvious degradated impurity was observed.

EXAMPLE 28 PHARMACEUTICAL COMPOSITION

| | |
|---|---|
| Polymorph I of N-(cyanomethyl)-4-(2-((4-(2',2',6',6'-d$_4$-morpholino)phenyl)amino)pyrimidin-4-yl)benzamide dihydrochloride (Examples 1-4) | 120 g |
| Starch | 180 g |
| Microcrystalline cellulose | 40 g |

According to the conventional method, the above materials were mixed and encapsulated into ordinary gelatin capsule to give 1,000 capsules.

EXAMPLE 29 PHARMACEUTICAL COMPOSITION

| | |
|---|---|
| Polymorph II of N-(cyanomethyl)-4-(2-((4-(2',2',6',6'-d$_4$-morpholino)phenyl)amino)pyrimidin-4-yl)benzamide dihydrochloride monohydrate (Examples 5-12) | 120 g |
| Starch | 180 g |
| Microcrystalline cellulose | 40 g |

According to the conventional method, the above materials were mixed and encapsulated into ordinary gelatin capsule to give 1,000 capsules.

EXAMPLE 30 PHARMACEUTICAL COMPOSITION

| | |
|---|---|
| Polymorph III of N-(cyanomethyl)-4-(2-((4-(2',2',6',6'-d$_4$-morpholino)phenyl)amino)pyrimidin-4-yl)benzamide hydrochloride (Examples 13-15) | 120 g |
| Starch | 180 g |
| Microcrystalline cellulose | 40 g |

According to the conventional method, the above materials were mixed and encapsulated into ordinary gelatin capsule to give 1,000 capsules.

EXAMPLE 31 PHARMACEUTICAL COMPOSITION

| | |
|---|---|
| Polymorph IV of N-(cyanomethyl)-4-(2-((4-(2',2',6',6'-d$_4$-morpholino)phenyl)amino)pyrimidin-4-yl)benzamide dihydrochloride (Examples 16-19) | 120 g |
| Starch | 180 g |
| Microcrystalline cellulose | 40 g |

According to the conventional method, the above materials were mixed and encapsulated into ordinary gelatin capsule to give 1,000 capsules.

EXAMPLE 32 PHARMACEUTICAL COMPOSITION

| | |
|---|---|
| Polymorph V of N-(cyanomethyl)-4-(2-((4-(2',2',6',6'-d$_4$-morpholino)phenyl)amino)pyrimidin-4-yl)benzamide (Example 20) | 120 g |
| Starch | 180 g |
| Microcrystalline cellulose | 40 g |

According to the conventional method, the above materials were mixed and encapsulated into ordinary gelatin capsule to give 1,000 capsules.

EXAMPLE 33 PHARMACEUTICAL COMPOSITION

| | |
|---|---|
| Polymorph VI of N-(cyanomethyl)-4-(2-((4-(2',2',6',6'-d$_4$-morpholino)phenyl)amino)pyrimidin-4-yl)benzamide (Example 21) | 120 g |
| Starch | 180 g |
| Microcrystalline cellulose | 40 g |

According to the conventional method, the above materials were mixed and encapsulated into ordinary gelatin capsule to give 1,000 capsules.

EXAMPLE 34 HYGROSCOPICITY TEST OF POLYMORPHS

The test was performed according to the guiding principles of drug's hygroscopic test (Chinese Pharmacopoeia 2010 edition, Appendix XIX J).

1. Take 4 dry glass weighing bottles with lids (60 mm of the outer diameter and 30 mm of the height). On the day before the test, the bottles were placed in a glass dryer ("constant temperature and humidity dryer") where a saturated ammonium sulfate solution was placed, and the glass dryer was placed in the bottom of a constant temperature and humidity box at 25° C.±1° C.

2. After each empty weighing bottle together with its lid were placed in the "constant temperature and humidity dryer" for 24 hours, stabilize precisely the weight of each unit by a set (one weighing bottle+its lid), recorded as m1.

3. A polymorph II sample was taken and tiled in a glass weighing bottle which had been weighed (the thickness of a sample was about 1 mm), and the bottle was covered, the weight of each weighing bottle (one weighing bottle+its lid+the sample) was precisely weighed, recorded as m2.

3. Each sample was placed in the "constant temperature and humidity dryer" for 24 h, and then the weight of each weighing bottle (one weighing bottle+its lid+the sample) was precisely weighed, recorded as m3.

4. The percentage of hygroscopicity weight increase of each sample was calculated (the formula was shown as follows), and it is defined as no or almost no hygroscopicity when the percentage of hygroscopicity weight increase is less than 0.2%. It is defined as slightly hygroscopicity when the percentage of hygroscopicity weight increase is equal or greater than 0.2%, but less than 2.0%.

$$\text{the percentage of weight increase} = [(m3-m2)/(m2-m1)] \times 100\%$$

According to the above steps, the hygroscopicity of the polymorph II of the present invention was tested. The results showed that the percentage of weight increase of polymorph II [(35.2826−35.2801)/(35.2801−34.2546)]×100%=0.24%. The result showed that polymorph II had slightly hygroscopicity.

Repeat Example 34 except that polymorph I, or was used instead of polymorph II. The results showed that various polymorphs of the present invention were very stable, substantially had no hygroscopicity, and only polymorph I had slightly hygroscopicity.

Therefore, polymorphs of the present invention are very suitable to be used in pharmaceutical compositions. Moreover, the polymorphs of the present invention, which are not prone to floating, easy for collection so that it is easy to avoid wasting and helpful to protect the health of operators in the manufacturing process of a drug, such as subpackage.

All literatures mentioned in the present application are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A polymorph, wherein the polymorph is a polymorph of compound I or a pharmaceutically acceptable salt thereof or a solvate thereof:

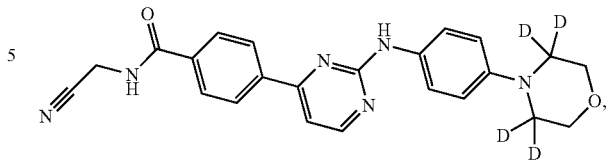

wherein the polymorph is selected from the group consisting of:

polymorph I of the hydrochloride of compound I, wherein the polymorph I has a characteristic X-ray powder diffraction spectrum comprising diffraction peaks at at least three diffraction angles (2θ) selected from the group consisting of 5.426±0.2°, 9.985±0.2°, 13.424±0.2°, 14.765±0.2°, 25.148±0.2° and 26.566±0.2°;

polymorph II of the solvate of the hydrochloride of compound I, wherein the polymorph II has a characteristic X-ray powder diffraction spectrum comprising diffraction peaks at at least three diffraction angles (2θ) selected from the group consisting of 17.249±0.2°, 19.224±0.2°, 23.885±0.2° and 29.488±0.2°, polymorph III of the hydrochloride of compound I, wherein the polymorph III has a characteristic X-ray powder diffraction spectrum comprising diffraction peaks at at least three diffraction angles (2θ) selected from the group consisting of 15.178±0.2°, 20.705±0.2°, 26.390±0.2° and 28.088±0.2°, polymorph IV of the hydrochloride of compound I, wherein the polymorph IV has a characteristic X-ray powder diffraction spectrum comprising diffraction peaks at at least three diffraction angles (2θ) selected from the group consisting of 12.493±0.2°, 14.447±0.2°, 17.627±0.2°, 19.519±0.2°, 23.231±0.2°, 23.805±0.2° and 24.831±0.2°, polymorph V of the compound I, wherein the polymorph V has a characteristic X-ray powder diffraction spectrum comprising diffraction peaks at at least three diffraction angles (2θ) selected from the group consisting of 13.621±0.2°, 18.634±0.2°, 20.331±0.2°, 21.675±0.2°, 22.621±0.2° and 28.048±0.2°, and polymorph VI of the compound I, wherein the polymorph VI has a characteristic X-ray powder diffraction spectrum comprising diffraction peaks at at least three diffraction angles (2θ) selected from the group consisting of 4.084±0.2°, 18.832±0.2°, 19.542±0.2°, 20.529±0.2°, and 26.468±0.2°.

2. The polymorph of claim 1, wherein the polymorph is polymorph I of the hydrochloride of compound I, wherein the polymorph I has a characteristic X-ray powder diffraction spectrum comprising diffraction peaks at diffraction angles (2θ) of 5.426±0.2°, 8.827±0.2°, 9.985±0.2°, 13.424±0.2°, 14.765±0.2°, 15.537±0.2°, 17.193±0.2°, 19.268±0.2°, 20.862±0.2°, 25.148±0.2°, 26.566±0.2°, and 30.282±0.2.

3. The polymorph of claim 1, wherein the polymorph is polymorph II of the solvate of the hydrochloride of compound I, wherein the polymorph II has a characteristic X-ray powder diffraction spectrum comprising diffraction peaks at diffraction angles (2θ) of 7.578±0.2°, 15.181±0.2°, 17.249±0.2°, 18.515±0.2°, 19.224±0.2°, 22.603±0.2°, 23.885±0.2°, 25.581±0.2°, 27.003±0.2° and 29.488±0.2°.

4. The polymorph of claim 1, wherein the polymorph is polymorph III of the hydrochloride of compound I, wherein the polymorph III has a characteristic X-ray powder diffraction spectrum comprising diffraction peaks at diffraction angles (2θ) of 13.305±0.2°, 15.178±0.2°, 16.204±0.2°, 16.953±0.2°, 18.809±0.2°, 20.073±0.2°, 20.705±0.2°, 22.937±0.2°, 25.958±0.2°, 26.390±0.2°, 28.088±0.2°, and 31.837±0.2°.

5. The polymorph of claim 1, wherein the polymorph is polymorph IV of the hydrochloride of compound I, wherein the polymorph IV has a characteristic X-ray powder diffraction spectrum comprising diffraction peaks at diffraction angles (2θ) of 4.422±0.2°, 12.493±0.2°, 12.986±0.2°, 14.447±0.2°, 17.074±0.2°, 17.627±0.2°, 19.519±0.2°, 22.344±0.2°, 23.231±0.2°, 23.805±0.2°, 24.396±0.2°, 24.831±0.2°, 25.778±0.2°, 28.166±0.2°, 28.738±0.2°, 29.607±0.2° and 31.741±0.2°.

6. The polymorph of claim 1, wherein the polymorph is polymorph V of the compound I, wherein the polymorph V has a characteristic X-ray powder diffraction spectrum comprising diffraction peaks at diffraction angles (2θ) of 7.263±0.2°, 13.621±0.2°, 17.647±0.2°, 18.634±0.2°, 20.331±0.2°, 21.179±0.2°, 21.675±0.2°, 22.621±0.2°, 23.509±0.2°, 24.852±0.2°, 25.148±0.2°, 27.179±0.2°, 28.048±0.2° and 30.181±0.2°.

7. The polymorph of claim 1, wherein the polymorph is polymorph VI of the compound I, wherein the polymorph VI has a characteristic X-ray powder diffraction spectrum comprising diffraction peaks at diffraction angles (2θ) of 4.084±0.2°, 12.277±0.2°, 17.589±0.2°, 18.832±0.2°, 19.542±0.2°, 20.032±0.2°, 20.529±0.2°, 21.003±0.2°, 24.870±0.2°, 26.468±0.2°, and 27.597±0.2°.

8. A pharmaceutical composition, comprising:
(a) the polymorph of claim 1; and
(b) a pharmaceutically acceptable carrier.

9. A method for preparing the polymorph of claim 1, comprising: salifying compound I with an acid and crystallizing in an inert solvent, or recrystallizing compound I or a pharmaceutically acceptable salt thereof or solvate thereof in an inert solvent, thereby obtaining the polymorph of claim 1.

10. A method for preparing a polymorph, wherein the polymorph is polymorph II of the solvate of the hydrochloride of compound I, wherein the polymorph II has a characteristic X-ray powder diffraction spectrum comprising diffraction peaks at at least three diffraction angles (2θ) selected from the group consisting of 17.249±0.2°, 19.224±0.2°, 23.885±0.2° and 29.488±0.2°, the method comprising steps of:

(1) mixing compound I and a first solvent to form a first solvent containing compound I:

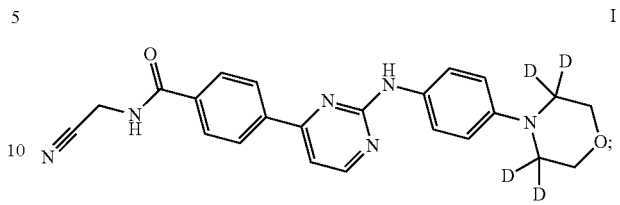

(2) adding hydrochloric acid and acetone to the first solvent to form a first mixture;
(3) stirring the first mixture, thereby precipitating a solid;
(4) separating and obtaining the solid precipitated from step (3);
(5) mixing the separated solid and the mixed solvent of acetone/water to form a second mixture; and
(6) separating crystallized polymorph II from the second mixture.

11. The method of claim 10, wherein in the first mixture, the molar ratio of compound I to the hydrochloric acid is about 1:1.8-1:3.

12. The method of claim 10, wherein in the mixed solvent of acetone/water, the volume ratio of acetone to water is 8:1-50:1.

13. The method of claim 10, wherein the first solvent is selected from the group consisting of: dimethylsulfoxide, N,N-dimethylformamide, N-methylpyrrolidone, and acetic acid, or a mixture thereof.

14. The method of claim 10, wherein the method has one or more characteristics selected from the group consisting of:
(a) in step (3), the temperature is 4-35° C.;
(b) in step (5), the temperature is 4-35° C.;
(c) in step (6), the temperature is 4-35° C.;
(d) in step (2), the hydrochloric acid and acetone are added in the form of an acetone solution of hydrochloric acid.

15. A method of inhibiting a non-receptor tyrosine kinase in a subject in need thereof, the method comprising administering to the subject the pharmaceutical composition of claim 8, wherein the non-receptor tyrosine kinase is a JAK kinase.

* * * * *